(12) United States Patent
Fuchs et al.

(10) Patent No.: US 8,222,264 B2
(45) Date of Patent: Jul. 17, 2012

(54) SUBSTITUTED AMINO-QUINAZOLINONES, MEDICAMENTS COMPRISING SAID COMPOUND, THEIR USE AND THEIR METHOD OF MANUFACTURE

(75) Inventors: Klaus Fuchs, Mittelbiberach (DE); Niklas Heine, Biberach (DE); Christian Eickmeier, Mittelbiberach (DE); Sandra Handschuh, Biberach (DE); Cornelia Dorner-Ciossek, Warthausen (DE); Stefan Hoerer, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 141 days.

(21) Appl. No.: 12/667,907

(22) PCT Filed: Jul. 3, 2008

(86) PCT No.: PCT/EP2008/058584
§ 371 (c)(1), (2), (4) Date: May 25, 2010

(87) PCT Pub. No.: WO2009/007300
PCT Pub. Date: Jan. 15, 2009

(65) Prior Publication Data
US 2010/0249158 A1    Sep. 30, 2010

(30) Foreign Application Priority Data
Jul. 6, 2007  (EP) .................................. 07111885

(51) Int. Cl.
*A61K 31/517* (2006.01)

(52) U.S. Cl. .................. 514/266.3; 514/266.4; 544/287; 544/292

(58) Field of Classification Search .................. 544/287, 544/292
See application file for complete search history.

(56) References Cited

FOREIGN PATENT DOCUMENTS

| WO | 2006/017836 A2 | 2/2006 |
| WO | 2006/017844 A1 | 2/2006 |
| WO | 2006/024932 A1 | 3/2006 |

OTHER PUBLICATIONS

International Search Report for PCT/EP2008/058584 mailed Apr. 1, 2009.

*Primary Examiner* — James O Wilson
*Assistant Examiner* — Brian McDowell
(74) *Attorney, Agent, or Firm* — Michael P. Morris; Edward S. Lazer

(57) ABSTRACT

The present invention relates to substituted amino-quinazolinones of general formula (I) wherein the groups $R^1$ to $R^{14}$ and A, are defined as in the specification and claims and the use thereof for the treatment of Alzheimer's disease (AD) and similar diseases.

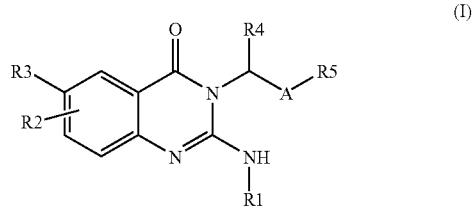

(I)

18 Claims, No Drawings

SUBSTITUTED AMINO-QUINAZOLINONES, MEDICAMENTS COMPRISING SAID COMPOUND, THEIR USE AND THEIR METHOD OF MANUFACTURE

This application is the national phase entry under 35 U.S.C. §371 of International Application No. PCT/EP2008/058584, filed Jul. 3, 2008, which claims priority to European Patent Application No. 07111885.5, filed Jul. 6, 2007, which are hereby incorporated by reference in their entireties.

TECHNICAL FIELD

This invention relates to substituted amino-quinazolinones and their use as R-secretase inhibitors, pharmaceutical compositions containing the same, and methods of using the same as agents for treatment and/or prevention of diseases and conditions in which the use of therapeutic effective amounts of compounds inhibiting β-secretase display a therapeutic benefit, e.g. in Alzheimer's disease.

BACKGROUND ART

EP 652 009 A1 describes inhibitors of aspartate protease which inhibit the production of beta-amyloid peptides in cell culture and in vivo.

WO 00/69262 discloses a beta-secretase and the use thereof in assays for finding potential active substances for the treatment of AD.

WO 01/00663 discloses memapsin 2 (human beta-secretase) as well as a recombinant catalytically active enzyme. Methods of identifying inhibitors of memapsin 2 are also described.

WO 01/00665 discloses inhibitors of memapsin 2 for the treatment of AD.

WO 03/057721 discloses substituted aminocarboxamides for the treatment of AD.

WO 05/004802 discloses substituted benzyl substituted N-alkyl-phenylcarboxamides for the treatment of AD.

The International patent applications WO 06/024932, WO 06/017836 and WO 06/017844 disclose substituted amino-quinazolines and their use as β-secretase inhibitors for the treatment of Alzheimer's disease.

At present there are no effective treatment methods capable of preventing, stopping or reversing AD.

Surprisingly, it has been found that the compounds of the present invention inhibit beta secretase-mediated cleavage of APP, are weakly basic, are only partially protonated at physiological conditions, show a high ability to overcome the blood/brain barrier and show improved selectivity against a variety of other biological targets.

DETAILED DESCRIPTION OF THE INVENTION

In a first aspect the present invention relates to substituted amino-quinazolinones of general formula 1

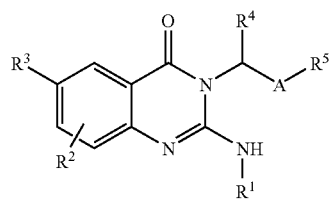

1 wherein
A is selected from the group GA.1 consisting of
a $C_1$-$C_3$-alkylene bridge, aryl-, heteroaryl- and heterocyclyl-, wherein the above-mentioned members of the group GA.1 may optionally be substituted independently of one another by one or more substituents selected from the group consisting of
fluorine, chlorine, bromine, HO—, NC—, $O_2N$—, $F_3C$—, $HF_2C$—, $FH_2C$—, $F_3C$—$CH_2$—, $R^{14}$—O—$C_{1-6}$-alkyl-, $C_{1-6}$-alkyl-, $C_{1-6}$-alkyl-O—, $F_3C$—O—, $HF_2C$—O—, $FH_2C$—O—, $(R^{13})_2N$—, $(R^{13})_2N$—$C_{1-3}$-alkyl-, and $(R^{13})_2$—N—CO—, $R^1$ is selected from the group GR1.1 consisting of H—, HO—, methyl-, ethyl-, $F_3C$—, $F_3C$—$CH_2$—, $H_3C$—O—, $H_3C$—$CH_2$—O—, $H_3C$—C(O)—, $(CH_3)_3C$—O—C(O)— and HC(O)—, $R^2$ is selected from the group GR2.1 consisting of
H—, fluorine, chlorine, bromine, HO—, NC—, $O_2N$—, $F_3C$—, $HF_2C$—, $FH_2C$—, $F_3C$—$CH_2$—, $F_3C$—O—, $HF_2C$—O—, $FH_2C$—O—, $C_{1-6}$-alkyl-, $C_{1-6}$-alkyl-S—, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, $R^{14}$—O—, $R^{14}$—O—$C_{1-3}$-alkyl-, $(R^{13})_2N$—, $(R^{13})_2$—N—CO—, $R^{13}$—CO—$(R^{13})N$—, $(R^{13})_2$—N—CO—$(R^{13})N$—, $R^{13}$—$SO_2$—$(R^{13})N$—, $(R^{13})_2N$—$SO_2$— and $R^{13}$—$SO_2$—,
wherein the above-mentioned members of the group GR2.1 may optionally be substituted independently of one another by one or more substituents selected from the group consisting of
fluorine, chlorine, bromine, HO—, NC—, $O_2N$—, $F_3C$—, $HF_2C$—, $FH_2C$—, HO—$C_{1-6}$-alkyl-, $C_{1-6}$-alkyl-, $C_{1-6}$-alkyl-O—, $(R^{13})_2N$—, $(R^{13})_2N$—$C_{1-3}$-alkyl-, and $(R^{13})_2N$—CO—, $R^3$ is selected from the group GR3.1 consisting of
H—, fluorine, chlorine, bromine, HO—, NC—, $F_3C$—, $HF_2C$—, $FH_2C$—, $F_3C$—$CH_2$—, $F_3C$—O—, $HF_2C$—O—, $FH_2C$—O—, $C_{1-6}$-alkyl-, $C_{1-6}$-alkyl-S—, $C_2$-$C_6$-alkenyl, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, $R^{12}$—O—, $R^{12}$—O—$C_{1-3}$-alkyl-, $R^{12}$—S—, $R^{12}$—CO—, $(R^{13})_2N$—, $(R^{13})_2$—N—CO—, $R^{13}$—CO—$(R^{13})N$—, $(R^{13})_2$N—CO—$(R^{13})N$—, $R^{13}$—$SO_2$—$(R^{13})N$—, $(R^{13})_2$N—$SO_2$— and $R^{13}$—$SO_2$—,
wherein the above-mentioned members of the group GR3.1 may optionally be substituted independently of one another by one or more substituents selected from the group consisting of
fluorine, chlorine, bromine, HO—, NC—, $O_2N$—, $F_3C$—, $HF_2C$—, $FH_2C$—, $F_3C$—$CH_2$—, $R^{14}$—O—, $R^{14}$—O—$C_{1-6}$-alkyl-, $C_{1-6}$-alkyl-, $(R^{13})_2N$—, $(R^{13})_2$N—$C_{1-3}$-alkyl-, and $(R^{13})_2$—N—CO—, $R^4$ is selected from the group GR4.1 consisting of
H—, fluorine, NC—, $F_3C$—, $HF_2C$—, $FH_2C$—, $F_3C$—$CH_2$—, $C_{1-6}$-alkyl-, $C_2$-$C_6$-alkenyl, $C_{1-6}$-alkyl-S—, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, $R^{14}$—O—, and $R^{14}$—O—$C_{1-3}$-alkyl-, wherein the above-mentioned members of the group GR4.1 may optionally be substituted independently of one another by one or more substituents selected from the group consisting of fluorine, chlorine, bromine, HO—, NC—, O$_2$N—, F$_3$C—, HF$_2$C—, FH$_2$C—, F$_3$C—CH$_2$—, HO—C$_{1-6}$-alkyl-, C$_{1-6}$-alkyl-, C$_{1-6}$-alkyl-O—, (R$^{13}$)$_2$N—, (R$^{13}$)$_2$N—C$_{1-3}$-alkyl-, and (R$^{13}$)$_2$—N—CO—, R$^5$ is selected from the group GR5.1 consisting of
R$^6$R$^7$N—CO—, R$^8$—CO—(R$^9$)N—, and R$^{10}$R$^{11}$—N—CO—(R$^9$)N—, R$^6$, R$^7$ are selected from the group GR6/11.1 consisting of
R$^8$, R$^9$H—, F$_3$C—, HF$_2$C—, FH$_2$C—, F$_3$C—CH$_2$—, C$_{1-6}$-alkyl-, C$_{2}$-C$_{6}$-alkenyl, C$_{1-6}$-alkyl-S—
R$^{10}$, R$^{11}$C$_{1-3}$-alkyl-, C$_{3-7}$-cycloalkyl-, C$_{3-7}$-cycloalkyl-C$_{1-6}$-alkyl-, aryl-, aryl-C$_{1-6}$-alkyl-, heterocyclyl-, heterocyclyl-C$_{1-6}$-alkyl-, heteroaryl-, heteroaryl-C$_{1-6}$-alkyl-, and
R$^{14}$—O—C$_{1-3}$-alkyl-,
wherein, if R$^6$ and R$^7$ or R$^{10}$ and R$^{11}$ are C$_{1-6}$-alkyl groups, those two C$_{1-6}$-alkyl groups bound to the same nitrogen atom of R$^5$ may be joined together forming, together with the nitrogen atom to which they are bound, a 3 to 7 membered heterocyclic ring, and wherein one of the —CH$_2$-groups of the heterocyclic ring formed by the R$^6$ and R$^7$ or R$^{10}$ and R$^{11}$ C$_{1-6}$-alkyl groups and the nitrogen atom of R$^5$ may be replaced by —O—, —S—, N—H, —N(C$_{3-6}$-cycloalkyl)-, —N(C$_{3-6}$-cycloalkyl-C$_{1-4}$-alkyl)- or —N(C$_{1-4}$-alkyl)- and
wherein the above-mentioned members of the group GR6/11.1 including the the heterocyclic ring formed by the R$^6$ and R$^7$ or R$^{10}$ and R$^{11}$C$_{1-6}$-alkyl groups and the nitrogen atom of R$^5$ may optionally be substituted independently of one another by one or more substituents selected from group GR6/11.S1 consisting of
fluorine, chlorine, bromine, HO—, NC—, O$_2$N—, F$_3$C—, HF$_2$C—, FH$_2$C—, HO—C$_{1-6}$-alkyl-, C$_{1-6}$-alkyl-, C$_{1-6}$-alkyl-O—, aryl-, (R$^{13}$)$_2$N—, (R$^{13}$)$_2$N—C$_{1-3}$-alkyl-, and (R$^{13}$)$_2$N—CO—
wherein the above-mentioned aryl of group GR6/11.S1 may optionally be substituted independently of one another by one or more substituents selected from group consisting of
fluorine, chlorine, bromine, NC—, F$_3$C—, HF$_2$C—, FH$_2$C—, F$_3$C—CH$_2$—, HO—C$_{1-6}$-alkyl-, C$_{1-6}$-alkyl-, and C$_{1-6}$-alkyl-O—, R$^{12}$ is selected from the group GR12.1 consisting of
F$_3$C—, HF$_2$C—, FH$_2$C—, F$_3$C—CH$_2$—, C$_{1-6}$-alkyl-, C$_{3-6}$-alkenyl-, C$_{1-6}$-alkyl-S—C$_{1-3}$-alkyl-, C$_{3-7}$-cycloalkyl-, C$_{3-7}$-cycloalkyl-C$_{1-6}$-alkyl-, aryl-, aryl-C$_{1-6}$-alkyl-, heterocyclyl-, heterocyclyl-C$_{1-6}$-alkyl-, heteroaryl-, and heteroaryl-C$_{1-6}$-alkyl-, wherein the above-mentioned members of the group GR12.1 may optionally be substituted independently of one another by one or more substituents selected from the group consisting of
fluorine, chlorine, bromine, R$^{14}$—O—, NC—, O$_2$N—, F$_3$C—, HF$_2$C—, FH$_2$C—, F$_3$C—CH$_2$—, R$^{14}$—O—C$_{1-6}$-alkyl-, C$_{1-6}$-alkyl-, (R$^{13}$)$_2$N—, (R$^{13}$)$_2$N—C$_{1-3}$-alkyl-, and (R$^{13}$)$_2$N—CO—.

R$^{13}$ is selected from the group GR13.1 consisting of
H—, F$_3$C—CH$_2$—, C$_{1-6}$-alkyl-, C$_{2-6}$-alkenyl-, C$_{3-7}$-cycloalkyl-, C$_{3-7}$-cycloalkyl-C$_{1-3}$-alkyl-, aryl-, aryl-C$_{1-3}$-alkyl-, heterocyclyl-, heterocyclyl-C$_{1-3}$-alkyl-, heteroaryl-, and heteroaryl-C$_{1-3}$-alkyl-,
wherein two C$_{1-6}$-alkyl groups bound to the same nitrogen atom may be joined together forming, together with the nitrogen atom to which they are bound, a 3 to 7 membered heterocyclic ring, and wherein one of the —CH$_2$— groups of the heterocyclic ring formed may be replaced by —O—, —S—, N—H, —N(C$_{3-6}$-cycloalkyl)-, —N(C$_{3-6}$-cycloalkyl-C$_{1-4}$-alkyl)- or —N(C$_{1-4}$-alkyl)- and
wherein the above-mentioned members of the group GR13.1 including the the heterocyclic ring formed may optionally be substituted independently of one another by one or more substituents selected from the group consisting of
fluorine, chlorine, bromine, HO—, NC—, O$_2$N—, F$_3$C—, HF$_2$C—, FH$_2$C—, F$_3$C—CH$_2$—, HO—C$_{1-6}$-alkyl-, C$_{1-6}$-alkyl-, and C$_{1-6}$-alkyl-O—.

R$^{14}$ is selected from the group GR14.1 consisting of
H—, F$_3$C—, HF$_2$C—, FH$_2$C—, F$_3$C—CH$_2$—, C$_{1-6}$-alkyl-, C$_{2-6}$-alkenyl-,C$_{3-7}$-cycloalkyl-, C$_{3-7}$-cyclyoalkyl-C$_{1-3}$-alkyl-, aryl-, aryl-C$_{1-3}$-alkyl-, heterocyclyl-, heterocyclyl-C$_{1-3}$-alkyl-, heteroaryl- and heteroaryl-C$_{1-3}$-alkyl-,
wherein the above-mentioned members of the group GR14.1 may optionally be substituted independently of one another by one or more substituents selected from the group consisting of
fluorine, chlorine, bromine, HO—, NC—, O$_2$N—, F$_3$C—, HF$_2$C—, FH$_2$C—, F$_3$C—CH$_2$—, HO—C$_{1-6}$-alkyl-, C$_{1-6}$-alkyl-, and C$_{1-6}$-alkyl-O—, and pharmaceutically acceptable salts thereof.

In a preferred embodiment of the present invention
A is selected from the group GA.2 consisting of
—CH2-, —CH2-CH2-, —CH2-CH2-CH2-, aryl-, and heteroaryl-,
wherein the above-mentioned members of the group GA.2 may optionally be substituted independently of one another by one or more substituents selected from the group consisting of
fluorine, chlorine, bromine, NC—, F$_3$C—, HF$_2$C—, FH$_2$C—, F$_3$C—CH$_2$—, F$_3$C—O—, HF$_2$C—O—, FH$_2$C—O—, H$_3$C—O—C$_{1-6}$-alkyl-, HO—C$_{1-6}$-alkyl-, C$_{1-6}$-alkyl-, and C$_{1-6}$-alkyl-O—.

In another preferred embodiment the present invention
A is selected from the group GA.3 consisting of
—CH2-CH2-, —CH2-CH2-CH2-, phenyl-, and pyridyl-,
wherein the above-mentioned members of the group GA.3 may optionally be substituted independently of one another by one or more substituents selected from the group consisting of
fluorine, chlorine, NC—, F$_3$C—, HF$_2$C—, FH$_2$C—, F$_3$C—CH$_2$—, F$_3$C—O—, HF$_2$C—O—, FH$_2$C—O—, H$_3$C—, and H$_3$C—O—.

In another preferred embodiment of the present invention
A is selected from the group GA.4 consisting of
—CH2-CH2-, and phenyl-,
wherein the above-mentioned members of the group GA.4 may optionally be substituted independently of one another by one or more substituents selected from the group consisting of
fluorine.

In another preferred embodiment of the present invention
A is selected from the group GA.5 consisting of
—CH2-CH2-,
wherein the above-mentioned members of the group GA.5 may optionally be substituted independently of one another by one or more substituents selected from the group consisting of
fluorine.

In another preferred embodiment of the present invention $R^1$ is selected from the group GR1.2 consisting of H—.

In another preferred embodiment of the present invention $R^2$ is selected from the group GR2.2 consisting of
H—, fluorine, chlorine, bromine, NC—, $F_3C$—, $HF_2C$—, $FH_2C$—, $F_3C$—$CH_2$—, $C_{1-6}$-alkyl-, $C_{1-6}$-alkyl-S—, $C_{3-7}$-cycloalkyl-, $C_{3-7}$-cycloalkyl-$C_{1-6}$-alkyl-, and $R^{14}$—O—.

In another preferred embodiment of the present invention $R^2$ is selected from the group GR2.3 consisting of
H—, fluorine, chlorine, bromine, NC—, $F_3C$—, $HF_2C$—, $FH_2C$—, $F_3C$—$CH_2$—, $C_{1-4}$-alkyl-, $C_{3-6}$-cycloalkyl-, $C_{3-6}$-cycloalkyl-$C_{1-4}$-alkyl-, and $C_{1-3}$-alkyl-O.

In another preferred embodiment of the present invention $R^2$ is selected from the group GR2.4 consisting of
H—, and fluorine, preferably H—.

In another preferred embodiment of the present invention $R^3$ is selected from the group GR3.2 consisting of
fluorine, chlorine, bromine, NC—, $F_3C$—, $HF_2C$—, $FH_2C$—, $F_3C$—$CH_2$—, $C_{1-6}$-alkyl-, $C_{1-6}$-alkyl-S—, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, $R^{12}$—O—, $R^{12}$—O—$C_{1-3}$-alkyl-, and $R^{12}$—CO—,
wherein the above-mentioned members of the group GR3.2 may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$—, HO—$C_{1-6}$-alkyl-, $C_{1-3}$-alkyl-, $C_{1-6}$-alkyl-O—, and $(R^{13})_2N$—CO—.

In another preferred embodiment of the present invention $R^3$ is selected from the group GR3.3 consisting of
Br, phenyl, heteroaryl-, and $R^{12}$—O—,
wherein the above-mentioned phenyl, heteroaryl-, and $R^{12}$—O— groups of GR3.3 may optionally be substituted independently of one another by one or more substituents selected from the group consisting of
fluorine, chlorine, bromine, NC—, $F_3C$—, $HF_2C$—, $FH_2C$—, $F_3C$—$CH_2$—, $C_{1-3}$-alkyl-, and $C_{1-3}$-alkyl-O—.

In another preferred embodiment of the present invention $R^3$ is selected from the group GR3.4 consisting of
Br, phenyl, and phenyl-O—,
wherein the above-mentioned phenyl, and phenyl-O— groups of GR3.4 may optionally be substituted independently of one another by one or more substituents selected from the group consisting of
fluorine, $H_3C$—$CH_2$—O— and $H_3C$—O—.

In another preferred embodiment of the present invention $R^3$ is selected from the group GR3.5 consisting of
Br, phenyl, and phenyl-O—,
wherein the above-mentioned phenyl, and phenyl-O— groups of GR3.5 may optionally be substituted independently of one another by one or more $H_3C$—$CH_2$—O—.

In another preferred embodiment of the present invention $R^4$ is selected from the group GR4.2 consisting of
H—, $F_3C$—, $HF_2C$—, $FH_2C$—, $F_3C$—$CH_2$—, $C_{1-6}$-alkyl-, $C_{1-6}$-alkyl-S—$C_{1-3}$-alkyl-, $C_{3-7}$-cycloalkyl-, $C_{3-7}$-cycloalkyl-$C_{1-3}$-alkyl-, aryl-, aryl-$C_{1-6}$-alkyl-, heterocyclyl-, heterocyclyl-$C_{1-3}$-alkyl-, heteroaryl-, heteroaryl-$C_{1-3}$-alkyl-, and $R^{14}$—O—$C_{1-3}$-alkyl-,
wherein the above-mentioned members of the group GR4.2 may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$—, HO—$C_{1-6}$-alkyl-, $C_{1-6}$-alkyl-, and $C_{1-6}$-alkyl-O—.

In another preferred embodiment of the present invention $R^4$ is selected from the group GR4.3 consisting of
H—, $C_{1-6}$-alkyl-, $C_{3-6}$-cycloalkyl-, $C_{3-6}$-cycloalkyl-$C_{1-3}$-alkyl-, aryl-, heterocyclyl-, heterocyclyl-$C_{1-3}$-alkyl-, heteroaryl-, and $C_{1-3}$-alkyl-O—$C_{1-3}$-alkyl-,
wherein the above-mentioned members of the group GR4.3 may optionally be substituted independently of one another by one or more substituents selected from the group consisting of
fluorine, chlorine, HO—, NC—, $F_3C$—, $HF_2C$—, $FH_2C$—, $F_3C$—$CH_2$—, $C_{1-3}$-alkyl-, and $C_{1-3}$-alkyl-O—.

In another preferred embodiment of the present invention $R^4$ is selected from the group GR4.4 consisting of
H—, $C_{1-6}$-alkyl-, $C_{3-6}$-cycloalkyl-, and $C_{3-6}$-cycloalkyl-$C_{1-2}$-alkyl-,
wherein the above-mentioned members of the group GR4.4 may optionally be substituted independently of one another by one or more substituents selected from the group consisting of
fluorine.

In another preferred embodiment of the present invention $R^4$ is selected from the group GR4.5 consisting of
$C_{3-6}$-cycloalkyl-,
wherein the above-mentioned members of the group GR4.5 may optionally be substituted independently of one another by one or more substituents selected from the group consisting of
fluorine.

In another preferred embodiment of the present invention $R^5$ is selected from the group GR5.2 consisting of
$R^6R^7N$—CO—.

In another preferred embodiment of the present invention $R^6$, $R^7$ are selected from the group GR6/11.2 consisting of
$R^8$, $R^9$H—, $F_3C$—, $HF_2C$—, $FH_2C$—, $F_3C$—$CH_2$—, $C_{1-6}$-alkyl-, $C_{1-6}$-alkyl-S—$C_{1-3}$-alkyl-, $C_{3-}$
$R^{10}$, $R^{11}$ $_7$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, and $R^{14}$—O—$C_{1-3}$-alkyl-,
wherein, if $R^6$ and $R^7$ or $R^{10}$ and $R^{11}$ are $C_{1-6}$-alkyl groups, those two $C_{1-6}$alkyl groups bound to the same nitrogen atom of $R^5$ may be joined together forming, together with the nitrogen atom to which they are bound, a 3 to 7 membered heterocyclic ring, and
wherein the above-mentioned members of the group GR6/11.2 including the the heterocyclic ring formed by the $R^6$ and $R^7$ or $R^{10}$ and $R^{11}$ $C_{1-6}$-alkyl groups and the nitrogen atom of $R^5$ may optionally be substituted independently of one another by one or more substituents selected from group GR6/11.S2 consisting of
fluorine, chlorine, bromine, HO—, NC—, $F_3C$—, $HF_2C$—, $FH_2C$—, $F_3C$—$CH_2$—, HO—$C_{1-6}$-alkyl-, $C_{1-6}$-alkyl-, $C_{1-6}$-alkyl-O—, and aryl-,
wherein the above-mentioned aryl of group GR6/11.S2 may optionally be substituted independently of one another by one or more substituents selected from group consisting of fluorine, chlorine, bromine, NC—, $F_3C$—, $HF_2C$—, $FH_2C$—, HO—$C_{1-3}$-alkyl-, $C_{1-3}$-alkyl-, and $C_{1-3}$-alkyl-O—.

In another preferred embodiment of the present invention $R^6$, $R^7$ are selected from the group GR6/7.3 consisting of
$C_{1-6}$-alkyl-, $C_{3-6}$-cycloalkyl-, and $C_{3-6}$-cycloalkyl-$C_{1-3}$-alkyl-,
wherein the above-mentioned members of the group GR6/7.3 may optionally be substituted independently of one another by one or more substituents selected from the group GR6/7.S3 consisting of
fluorine, HO—, NC—, $C_{1-3}$-alkyl-, and $C_{1-3}$-alkyl-O—.

In another preferred embodiment of the present invention $R^6$ are selected from the group GR6.4 consisting of
$C_{5-6}$-cycloalkyl-,
wherein the above-mentioned members of the group GR6.4 may optionally be substituted independently of one another by one or more substituents selected from the group consisting of
fluorine, and $H_3C$—, preferably fluorine.

In another preferred embodiment of the present invention $R^7$ are selected from the group GR7.4 consisting of
$C_{1-4}$-alkyl-,
wherein the above-mentioned members of the group GR7.4 may optionally be substituted independently of one another by one or more substituents selected from the group consisting of
fluorine, HO—, and $H_3C$—O—.

In another preferred embodiment of the present invention $R^7$ are selected from the group GR7.5 consisting of
methyl-,
wherein the above-mentioned members of the group GR7.5 may optionally be substituted independently of one another by one or more substituents selected from the group consisting of
fluorine, HO—, and $H_3C$—O—.

In another preferred embodiment of the present invention $R^8$ are selected from the group GR8.3 consisting of
$C_{1-6}$-alkyl-, $C_{3-6}$-cycloalkyl-, and $C_{3-6}$-cycloalkyl-$C_{1-3}$-alkyl-,
wherein the above-mentioned members of the group GR8.3 may optionally be substituted independently of one another by one or more substituents selected from the group consisting of
fluorine, HO—, NC—, and $H_3C$—.

In another preferred embodiment of the present invention $R^8$ are selected from the group GR8.4 consisting of
$C_{3-6}$-alkyl-, and $C_{5-6}$-cycloalkyl-,
wherein the above-mentioned members of the group GR8.4 may optionally be substituted independently of one another by one or more substituents selected from the group consisting of
fluorine, and $H_3C$—.

In another preferred embodiment of the present invention $R^9$ are selected from the group GR9.3 consisting of
H—, $F_3C$—$CH_2$—, $C_{1-6}$-alkyl-,
wherein the above-mentioned members of the group GR9.3 may optionally be substituted independently of one another by one or more substituents selected from group GR9.S3 consisting of
fluorine.

In another preferred embodiment of the present invention $R^9$ are selected from the group GR9.4 consisting of
H—.

In another preferred embodiment of the present invention $R^{12}$ is selected from the group GR12.2 consisting of
$F_3C$—, $HF_2C$—, $FH_2C$—, $C_{1-6}$-alkyl-, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, and heteroaryl-$C_{1-6}$-alkyl-,
wherein the above-mentioned members of the group GR12.2 may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$—, HO—$C_{1-3}$-alkyl-, $C_{1-3}$-alkyl-, and $C_{1-3}$-alkyl-O—.

In another preferred embodiment of the present invention $R^{12}$ is selected from the group GR12.3 consisting of
$C_{1-6}$-alkyl-, $C_{3-7}$-cycloalkyl-, $C_{3-7}$-cycloalkyl-$C_{1-6}$-alkyl-, aryl-, heterocyclyl-, and heteroaryl-
wherein the above-mentioned members of the group GR12.3 may optionally be substituted independently of one another by one or more substituents selected from the group consisting of
fluorine, chlorine, bromine, NC—, $F_3C$—, $HF_2C$—, $FH_2C$—, $F_3C$—$CH_2$—, $C_{1-3}$-alkyl-, and $C_{1-3}$-alkyl-O—.

In another preferred embodiment of the present invention $R^{12}$ is selected from the group GR12.4 consisting of phenyl-, and heteroaryl-
wherein the above-mentioned members of the group GR12.4 may optionally be substituted independently of one another by one or more substituents selected from the group consisting of
fluorine, chlorine, bromine, NC—, $F_3C$—, $HF_2C$—, $FH_2C$—, $F_3C$—$CH_2$—, $C_{1-3}$-alkyl-, and $C_{1-3}$-alkyl-O—.

In another preferred embodiment of the present invention $R^{13}$ is selected from the group GR13.2 consisting of
H—, $F_3C$—$CH_2$—, $C_{1-6}$-alkyl-, $C_{3-7}$-cycloalkyl-, $C_{3-7}$-cycloalkyl-$C_{1-3}$-alkyl-, aryl-, aryl-$C_{1-3}$-alkyl-, heterocyclyl-, heterocyclyl-$C_{1-3}$-alkyl-, heteroaryl-, and heteroaryl-$C_{1-3}$-alkyl-,
wherein two $C_{1-6}$-alkyl groups bound to the same nitrogen atom may be joined together forming, together with the nitrogen atom to which they are bound, a 3 to 7 membered heterocyclic ring, and
wherein the above-mentioned members of the group GR13.2 may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$—, HO—$C_{1-6}$-alkyl-, $C_{1-6}$-alkyl-, and $C_{1-6}$-alkyl-O—.

In another preferred embodiment of the present invention $R^{13}$ is selected from the group GR13.3 consisting of
H—, $F_3C$—$CH_2$—, $C_{1-6}$-alkyl-, $C_{3-7}$-cycloalkyl- and $C_{3-7}$-cycloalkyl-$C_{1-3}$-alkyl-,
wherein two $C_{1-6}$-alkyl groups bound to the same nitrogen atom may be joined together forming, together with the nitrogen atom to which they are bound, a 3 to 7 membered heterocyclic ring, and
wherein the above-mentioned members of the group GR13.3 may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$—, HO—$C_{1-6}$-alkyl-, $C_{1-6}$-alkyl-, and $C_{1-6}$-alkyl-O—.

In another preferred embodiment of the present invention $R^{13}$ is selected from the group GR13.4 consisting of
H—, $C_{1-6}$-alkyl-, wherein the above-mentioned members of the group GR13.4 may optionally be substituted independently of one another by one or more substituents selected from the group consisting of
fluorine.

In another preferred embodiment of the present invention $R^{14}$ is selected from the group GR14.2 consisting of H—, $F_3C$—, $HF_2C$—, $FH_2C$—, $F_3C$—$CH_2$—, $C_{1-6}$-alkyl-, $C_{3-7}$-cycloalkyl-, $C_{3-7}$-cyclyoalkyl-$C_{1-3}$-alkyl-, aryl-, aryl-$C_{1-3}$-alkyl-, heterocyclyl-, heterocyclyl-$C_{1-3}$-alkyl-, heteroaryl- and heteroaryl-$C_{1-3}$-alkyl-, wherein the above-mentioned members of the group GR14.2 may optionally be substituted independently of one another by one or more substituents selected from the group consisting of fluorine, chlorine, bromine, HO—, NC—, $F_3C$—, $HF_2C$—, $FH_2C$—, $F_3C$—$CH_2$—, $C_{1-3}$-alkyl-, and $C_{1-6}$-alkyl-O—, In another preferred embodiment of the present invention $R^{14}$ is selected from the group GR14.3 consisting of H—, $C_{1-6}$-alkyl-, $C_{3-7}$-cycloalkyl-, $C_{3-7}$-cyclyoalkyl-$C_{1-3}$-alkyl-, wherein the above-mentioned members of the group GR14.3 may optionally be substituted independently of one another by one or more substituents selected from the group consisting of fluorine, chlorine, bromine, HO—, NC—, $C_{1-3}$-alkyl-, and $C_{1-6}$-alkyl-O—, In another preferred embodiment of the present invention $R^{14}$ is selected from the group GR14.4 consisting of $C_{1-6}$-alkyl-, wherein the above-mentioned members of the group GR14.4 may optionally be substituted independently of one another by one or more substituents selected from the group consisting of fluorine, Any and each of the above definitions for A and $R^1$ to $R^{14}$ may be combined with each other.

The following table represents further embodiments 1.a to 16.f of the compounds of formula 1 including their pharmaceutically acceptable salts:

Particularly preferred compounds according to the invention are compounds according to formula 1A,

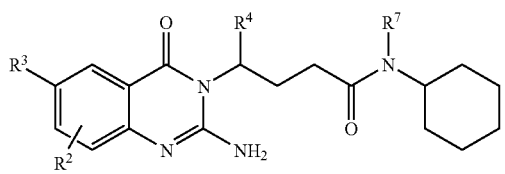

1A wherein $R^2$, $R^3$, $R^4$, $R^7$, $R^{12}$, $R^{13}$ and $R^{14}$ have the meanings given hereinbefore and pharmaceutically acceptable salts thereof.

More preferred are such compounds of formula 1A wherein $R^2$, $R^3$, $R^4$, $R^7$ and $R^{12}$, are defined as in table 1 below and pharmaceutically acceptable salts thereof.

TABLE 1

| Group No. | $R^2$ | $R^3$ | $R^4$ | $R^7$ | $R^{12}$ |
|---|---|---|---|---|---|
| 1. a | GR2.3 | GR3.3 | GR4.3 | GR6/7.3 | GR12.3 |
| 2. a | GR2.3 | GR3.3 | GR4.3 | GR6/7.3 | GR12.4 |
| 3. a | GR2.3 | GR3.3 | GR4.3 | GR7.4 | GR12.3 |

TABLE 1-continued

| Group No. | $R^2$ | $R^3$ | $R^4$ | $R^7$ | $R^{12}$ |
|---|---|---|---|---|---|
| 4. a | GR2.3 | GR3.3 | GR4.3 | GR7.4 | GR12.4 |
| 5. a | GR2.3 | GR3.3 | GR4.3 | GR7.5 | GR12.3 |
| 6. a | GR2.3 | GR3.3 | GR4.3 | GR7.5 | GR12.4 |
| 7. a | GR2.3 | GR3.3 | GR4.4 | GR6/7.3 | GR12.3 |
| 8. a | GR2.3 | GR3.3 | GR4.4 | GR6/7.3 | GR12.4 |
| 9. a | GR2.3 | GR3.3 | GR4.4 | GR7.4 | GR12.3 |
| 10. a | GR2.3 | GR3.3 | GR4.4 | GR7.4 | GR12.4 |
| 11. a | GR2.3 | GR3.3 | GR4.4 | GR7.5 | GR12.3 |
| 12. a | GR2.3 | GR3.3 | GR4.4 | GR7.5 | GR12.4 |
| 13. a | GR2.3 | GR3.3 | GR4.5 | GR6/7.3 | GR12.3 |
| 14. a | GR2.3 | GR3.3 | GR4.5 | GR6/7.3 | GR12.4 |
| 15. a | GR2.3 | GR3.3 | GR4.5 | GR7.4 | GR12.3 |
| 16. a | GR2.3 | GR3.3 | GR4.5 | GR7.4 | GR12.4 |
| 17. a | GR2.3 | GR3.3 | GR4.5 | GR7.5 | GR12.3 |
| 18. a | GR2.3 | GR3.3 | GR4.5 | GR7.5 | GR12.4 |
| 19. a | GR2.3 | GR3.4 | GR4.3 | GR6/7.3 | GR12.3 |
| 20. a | GR2.3 | GR3.4 | GR4.3 | GR6/7.3 | GR12.4 |
| 21. a | GR2.3 | GR3.4 | GR4.3 | GR7.4 | GR12.3 |
| 22. a | GR2.3 | GR3.4 | GR4.3 | GR7.4 | GR12.4 |
| 23. a | GR2.3 | GR3.4 | GR4.3 | GR7.5 | GR12.3 |
| 24. a | GR2.3 | GR3.4 | GR4.3 | GR7.5 | GR12.4 |
| 25. a | GR2.3 | GR3.4 | GR4.4 | GR6/7.3 | GR12.3 |
| 26. a | GR2.3 | GR3.4 | GR4.4 | GR6/7.3 | GR12.4 |
| 27. a | GR2.3 | GR3.4 | GR4.4 | GR7.4 | GR12.3 |
| 28. a | GR2.3 | GR3.4 | GR4.4 | GR7.4 | GR12.4 |
| 29. a | GR2.3 | GR3.4 | GR4.4 | GR7.5 | GR12.3 |
| 30. a | GR2.3 | GR3.4 | GR4.4 | GR7.5 | GR12.4 |
| 31. a | GR2.3 | GR3.4 | GR4.5 | GR6/7.3 | GR12.3 |
| 32. a | GR2.3 | GR3.4 | GR4.5 | GR6/7.3 | GR12.4 |
| 33. a | GR2.3 | GR3.4 | GR4.5 | GR7.4 | GR12.3 |
| 34. a | GR2.3 | GR3.4 | GR4.5 | GR7.4 | GR12.4 |
| 35. a | GR2.3 | GR3.4 | GR4.5 | GR7.5 | GR12.3 |
| 36. a | GR2.3 | GR3.4 | GR4.5 | GR7.5 | GR12.4 |
| 37. a | GR2.3 | GR3.5 | GR4.3 | GR6/7.3 | GR12.3 |
| 38. a | GR2.3 | GR3.5 | GR4.3 | GR6/7.3 | GR12.4 |
| 39. a | GR2.3 | GR3.5 | GR4.3 | GR7.4 | GR12.3 |
| 40. a | GR2.3 | GR3.5 | GR4.3 | GR7.4 | GR12.4 |
| 41. a | GR2.3 | GR3.5 | GR4.3 | GR7.5 | GR12.3 |
| 42. a | GR2.3 | GR3.5 | GR4.3 | GR7.5 | GR12.4 |
| 43. a | GR2.3 | GR3.5 | GR4.4 | GR6/7.3 | GR12.3 |
| 44. a | GR2.3 | GR3.5 | GR4.4 | GR6/7.3 | GR12.4 |
| 45. a | GR2.3 | GR3.5 | GR4.4 | GR7.4 | GR12.3 |
| 46. a | GR2.3 | GR3.5 | GR4.4 | GR7.4 | GR12.4 |
| 47. a | GR2.3 | GR3.5 | GR4.4 | GR7.5 | GR12.3 |
| 48. a | GR2.3 | GR3.5 | GR4.4 | GR7.5 | GR12.4 |
| 49. a | GR2.3 | GR3.5 | GR4.5 | GR6/7.3 | GR12.3 |
| 50. a | GR2.3 | GR3.5 | GR4.5 | GR6/7.3 | GR12.4 |
| 51. a | GR2.3 | GR3.5 | GR4.5 | GR7.4 | GR12.3 |
| 52. a | GR2.3 | GR3.5 | GR4.5 | GR7.4 | GR12.4 |
| 53. a | GR2.3 | GR3.5 | GR4.5 | GR7.5 | GR12.3 |
| 54. a | GR2.3 | GR3.5 | GR4.5 | GR7.5 | GR12.4 |
| 55. a | GR2.4 | GR3.3 | GR4.3 | GR6/7.3 | GR12.3 |
| 56. a | GR2.4 | GR3.3 | GR4.3 | GR6/7.3 | GR12.4 |
| 57. a | GR2.4 | GR3.3 | GR4.3 | GR7.4 | GR12.3 |
| 58. a | GR2.4 | GR3.3 | GR4.3 | GR7.4 | GR12.4 |
| 59. a | GR2.4 | GR3.3 | GR4.3 | GR7.5 | GR12.3 |
| 60. a | GR2.4 | GR3.3 | GR4.3 | GR7.5 | GR12.4 |
| 61. a | GR2.4 | GR3.3 | GR4.4 | GR6/7.3 | GR12.3 |
| 62. a | GR2.4 | GR3.3 | GR4.4 | GR6/7.3 | GR12.4 |
| 63. a | GR2.4 | GR3.3 | GR4.4 | GR7.4 | GR12.3 |
| 64. a | GR2.4 | GR3.3 | GR4.4 | GR7.4 | GR12.4 |
| 65. a | GR2.4 | GR3.3 | GR4.4 | GR7.5 | GR12.3 |
| 66. a | GR2.4 | GR3.3 | GR4.4 | GR7.5 | GR12.4 |
| 67. a | GR2.4 | GR3.3 | GR4.5 | GR6/7.3 | GR12.3 |
| 68. a | GR2.4 | GR3.3 | GR4.5 | GR6/7.3 | GR12.4 |
| 69. a | GR2.4 | GR3.3 | GR4.5 | GR7.4 | GR12.3 |
| 70. a | GR2.4 | GR3.3 | GR4.5 | GR7.4 | GR12.4 |
| 71. a | GR2.4 | GR3.3 | GR4.5 | GR7.5 | GR12.3 |
| 72. a | GR2.4 | GR3.3 | GR4.5 | GR7.5 | GR12.4 |
| 73. a | GR2.4 | GR3.4 | GR4.3 | GR6/7.3 | GR12.3 |
| 74. a | GR2.4 | GR3.4 | GR4.3 | GR6/7.3 | GR12.4 |
| 75. a | GR2.4 | GR3.4 | GR4.3 | GR7.4 | GR12.3 |
| 76. a | GR2.4 | GR3.4 | GR4.3 | GR7.4 | GR12.4 |
| 77. a | GR2.4 | GR3.4 | GR4.3 | GR7.5 | GR12.3 |
| 78. a | GR2.4 | GR3.4 | GR4.3 | GR7.5 | GR12.4 |
| 79. a | GR2.4 | GR3.4 | GR4.4 | GR6/7.3 | GR12.3 |
| 80. a | GR2.4 | GR3.4 | GR4.4 | GR6/7.3 | GR12.4 |

TABLE 1-continued

| Group No. | R² | R³ | R⁴ | R⁷ | R¹² |
|---|---|---|---|---|---|
| 81. a | GR2.4 | GR3.4 | GR4.4 | GR7.4 | GR12.3 |
| 82. a | GR2.4 | GR3.4 | GR4.4 | GR7.4 | GR12.4 |
| 83. a | GR2.4 | GR3.4 | GR4.4 | GR7.5 | GR12.3 |
| 84. a | GR2.4 | GR3.4 | GR4.4 | GR7.5 | GR12.4 |
| 85. a | GR2.4 | GR3.4 | GR4.5 | GR6/7.3 | GR12.3 |
| 86. a | GR2.4 | GR3.4 | GR4.5 | GR6/7.3 | GR12.4 |
| 87. a | GR2.4 | GR3.4 | GR4.5 | GR7.4 | GR12.3 |
| 88. a | GR2.4 | GR3.4 | GR4.5 | GR7.4 | GR12.4 |
| 89. a | GR2.4 | GR3.4 | GR4.5 | GR7.5 | GR12.3 |
| 90. a | GR2.4 | GR3.4 | GR4.5 | GR7.5 | GR12.4 |
| 91. a | GR2.4 | GR3.5 | GR4.3 | GR6/7.3 | GR12.3 |
| 92. a | GR2.4 | GR3.5 | GR4.3 | GR6/7.3 | GR12.4 |
| 93. a | GR2.4 | GR3.5 | GR4.3 | GR7.4 | GR12.3 |
| 94. a | GR2.4 | GR3.5 | GR4.3 | GR7.4 | GR12.4 |
| 95. a | GR2.4 | GR3.5 | GR4.3 | GR7.5 | GR12.3 |
| 96. a | GR2.4 | GR3.5 | GR4.3 | GR7.5 | GR12.4 |
| 97. a | GR2.4 | GR3.5 | GR4.4 | GR6/7.3 | GR12.3 |
| 98. a | GR2.4 | GR3.5 | GR4.4 | GR6/7.3 | GR12.4 |
| 99. a | GR2.4 | GR3.5 | GR4.4 | GR7.4 | GR12.3 |
| 100. a | GR2.4 | GR3.5 | GR4.4 | GR7.4 | GR12.4 |
| 101. a | GR2.4 | GR3.5 | GR4.4 | GR7.5 | GR12.3 |
| 102. a | GR2.4 | GR3.5 | GR4.4 | GR7.5 | GR12.4 |
| 103. a | GR2.4 | GR3.5 | GR4.5 | GR6/7.3 | GR12.3 |
| 104. a | GR2.4 | GR3.5 | GR4.5 | GR6/7.3 | GR12.4 |
| 105. a | GR2.4 | GR3.5 | GR4.5 | GR7.4 | GR12.3 |
| 106. a | GR2.4 | GR3.5 | GR4.5 | GR7.4 | GR12.4 |
| 107. a | GR2.4 | GR3.5 | GR4.5 | GR7.5 | GR12.3 |
| 108. a | GR2.4 | GR3.5 | GR4.5 | GR7.5 | GR12.4 |

Also particularly preferred compounds according to the invention are compounds according to formula 1B,

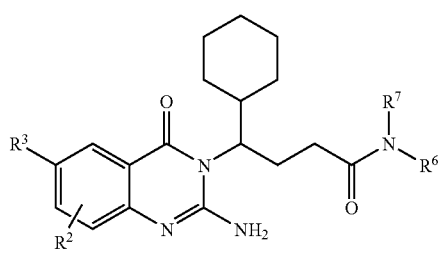

1B wherein
$R^2$, $R^3$, $R^6$, $R^7$, $R^{12}$, $R^{13}$ and $R^{14}$ have the meanings given hereinbefore and pharmaceutically acceptable salts thereof.

More preferred are such compounds of formula 1B wherein $R^2$, $R^3$, $R^6$, $R^7$ and $R^{12}$, are defined as in table 2 below and pharmaceutically acceptable salts thereof.

TABLE 2

| Group No. | R² | R³ | R⁶ | R⁷ | R¹² |
|---|---|---|---|---|---|
| 1. b | GR2.3 | GR3.3 | GR6/7.3 | GR6/7.3 | GR12.3 |
| 2. b | GR2.3 | GR3.3 | GR6/7.3 | GR6/7.3 | GR12.4 |
| 3. b | GR2.3 | GR3.3 | GR6/7.3 | GR7.4 | GR12.3 |
| 4. b | GR2.3 | GR3.3 | GR6/7.3 | GR7.4 | GR12.4 |
| 5. b | GR2.3 | GR3.3 | GR6/7.3 | GR7.5 | GR12.3 |
| 6. b | GR2.3 | GR3.3 | GR6/7.3 | GR7.5 | GR12.4 |
| 7. b | GR2.3 | GR3.3 | GR6.4 | GR6/7.3 | GR12.3 |
| 8. b | GR2.3 | GR3.3 | GR6.4 | GR6/7.3 | GR12.4 |
| 9. b | GR2.3 | GR3.3 | GR6.4 | GR7.4 | GR12.3 |
| 10. b | GR2.3 | GR3.3 | GR6.4 | GR7.4 | GR12.4 |
| 11. b | GR2.3 | GR3.3 | GR6.4 | GR7.5 | GR12.3 |
| 12. b | GR2.3 | GR3.3 | GR6.4 | GR7.5 | GR12.4 |
| 13. b | GR2.3 | GR3.4 | GR6/7.3 | GR6/7.3 | GR12.3 |
| 14. b | GR2.3 | GR3.4 | GR6/7.3 | GR6/7.3 | GR12.4 |
| 15. b | GR2.3 | GR3.4 | GR6/7.3 | GR7.4 | GR12.3 |
| 16. b | GR2.3 | GR3.4 | GR6/7.3 | GR7.4 | GR12.4 |
| 17. b | GR2.3 | GR3.4 | GR6/7.3 | GR7.5 | GR12.3 |
| 18. b | GR2.3 | GR3.4 | GR6/7.3 | GR7.5 | GR12.4 |
| 19. b | GR2.3 | GR3.4 | GR6.4 | GR6/7.3 | GR12.3 |
| 20. b | GR2.3 | GR3.4 | GR6.4 | GR6/7.3 | GR12.4 |
| 21. b | GR2.3 | GR3.4 | GR6.4 | GR7.4 | GR12.3 |
| 22. b | GR2.3 | GR3.4 | GR6.4 | GR7.4 | GR12.4 |
| 23. b | GR2.3 | GR3.4 | GR6.4 | GR7.5 | GR12.3 |
| 24. b | GR2.3 | GR3.4 | GR6.4 | GR7.5 | GR12.4 |
| 25. b | GR2.3 | GR3.5 | GR6/7.3 | GR6/7.3 | GR12.3 |
| 26. b | GR2.3 | GR3.5 | GR6/7.3 | GR6/7.3 | GR12.4 |
| 27. b | GR2.3 | GR3.5 | GR6/7.3 | GR7.4 | GR12.3 |
| 28. b | GR2.3 | GR3.5 | GR6/7.3 | GR7.4 | GR12.4 |
| 29. b | GR2.3 | GR3.5 | GR6/7.3 | GR7.5 | GR12.3 |
| 30. b | GR2.3 | GR3.5 | GR6/7.3 | GR7.5 | GR12.4 |
| 31. b | GR2.3 | GR3.5 | GR6.4 | GR6/7.3 | GR12.3 |
| 32. b | GR2.3 | GR3.5 | GR6.4 | GR6/7.3 | GR12.4 |
| 33. b | GR2.3 | GR3.5 | GR6.4 | GR7.4 | GR12.3 |
| 34. b | GR2.3 | GR3.5 | GR6.4 | GR7.4 | GR12.4 |
| 35. b | GR2.3 | GR3.5 | GR6.4 | GR7.5 | GR12.3 |
| 36. b | GR2.3 | GR3.5 | GR6.4 | GR7.5 | GR12.4 |
| 37. b | GR2.4 | GR3.3 | GR6/7.3 | GR6/7.3 | GR12.3 |
| 38. b | GR2.4 | GR3.3 | GR6/7.3 | GR6/7.3 | GR12.4 |
| 39. b | GR2.4 | GR3.3 | GR6/7.3 | GR7.4 | GR12.3 |
| 40. b | GR2.4 | GR3.3 | GR6/7.3 | GR7.4 | GR12.4 |
| 41. b | GR2.4 | GR3.3 | GR6/7.3 | GR7.5 | GR12.3 |
| 42. b | GR2.4 | GR3.3 | GR6/7.3 | GR7.5 | GR12.4 |
| 43. b | GR2.4 | GR3.3 | GR6.4 | GR6/7.3 | GR12.3 |
| 44. b | GR2.4 | GR3.3 | GR6.4 | GR6/7.3 | GR12.4 |
| 45. b | GR2.4 | GR3.3 | GR6.4 | GR7.4 | GR12.3 |
| 46. b | GR2.4 | GR3.3 | GR6.4 | GR7.4 | GR12.4 |
| 47. b | GR2.4 | GR3.3 | GR6.4 | GR7.5 | GR12.3 |
| 48. b | GR2.4 | GR3.3 | GR6.4 | GR7.5 | GR12.4 |
| 49. b | GR2.4 | GR3.4 | GR6/7.3 | GR6/7.3 | GR12.3 |
| 50. b | GR2.4 | GR3.4 | GR6/7.3 | GR6/7.3 | GR12.4 |
| 51. b | GR2.4 | GR3.4 | GR6/7.3 | GR7.4 | GR12.3 |
| 52. b | GR2.4 | GR3.4 | GR6/7.3 | GR7.4 | GR12.4 |
| 53. b | GR2.4 | GR3.4 | GR6/7.3 | GR7.5 | GR12.3 |
| 54. b | GR2.4 | GR3.4 | GR6/7.3 | GR7.5 | GR12.4 |
| 55. b | GR2.4 | GR3.4 | GR6.4 | GR6/7.3 | GR12.3 |
| 56. b | GR2.4 | GR3.4 | GR6.4 | GR6/7.3 | GR12.4 |
| 57. b | GR2.4 | GR3.4 | GR6.4 | GR7.4 | GR12.3 |
| 58. b | GR2.4 | GR3.4 | GR6.4 | GR7.4 | GR12.4 |
| 59. b | GR2.4 | GR3.4 | GR6.4 | GR7.5 | GR12.3 |
| 60. b | GR2.4 | GR3.4 | GR6.4 | GR7.5 | GR12.4 |
| 61. b | GR2.4 | GR3.5 | GR6/7.3 | GR6/7.3 | GR12.3 |
| 62. b | GR2.4 | GR3.5 | GR6/7.3 | GR6/7.3 | GR12.4 |
| 63. b | GR2.4 | GR3.5 | GR6/7.3 | GR7.4 | GR12.3 |
| 64. b | GR2.4 | GR3.5 | GR6/7.3 | GR7.4 | GR12.4 |
| 65. b | GR2.4 | GR3.5 | GR6/7.3 | GR7.5 | GR12.3 |
| 66. b | GR2.4 | GR3.5 | GR6/7.3 | GR7.5 | GR12.4 |
| 67. b | GR2.4 | GR3.5 | GR6.4 | GR6/7.3 | GR12.3 |
| 68. b | GR2.4 | GR3.5 | GR6.4 | GR6/7.3 | GR12.4 |
| 69. b | GR2.4 | GR3.5 | GR6.4 | GR7.4 | GR12.3 |
| 70. b | GR2.4 | GR3.5 | GR6.4 | GR7.4 | GR12.4 |
| 71. b | GR2.4 | GR3.5 | GR6.4 | GR7.5 | GR12.3 |
| 72. b | GR2.4 | GR3.5 | GR6.4 | GR7.5 | GR12.4 |

Also particularly preferred compounds according to the invention are compounds according to formula 1C,

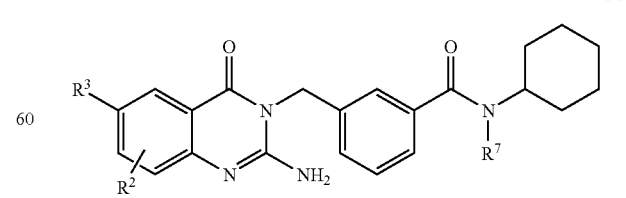

1C wherein
$R^2$, $R^3$, $R^7$, $R^{12}$, $R^{13}$ and $R^{14}$ have the meanings given hereinbefore and pharmaceutically acceptable salts thereof.

More preferred are such compounds of formula 1c wherein $R^2$, $R^3$, $R^7$ and $R^{12}$, are defined as in table 3 below and pharmaceutically acceptable salts thereof.

TABLE 3

| Group No. | $R^2$ | $R^3$ | $R^7$ | $R^{12}$ |
|---|---|---|---|---|
| 1. c | GR2.3 | GR3.3 | GR6/7.3 | GR12.3 |
| 2. c | GR2.3 | GR3.3 | GR6/7.3 | GR12.4 |
| 3. c | GR2.3 | GR3.3 | GR7.4 | GR12.3 |
| 4. c | GR2.3 | GR3.3 | GR7.4 | GR12.4 |
| 5. c | GR2.3 | GR3.3 | GR7.5 | GR12.3 |
| 6. c | GR2.3 | GR3.3 | GR7.5 | GR12.4 |
| 7. c | GR2.3 | GR3.4 | GR6/7.3 | GR12.3 |
| 8. c | GR2.3 | GR3.4 | GR6/7.3 | GR12.4 |
| 9. c | GR2.3 | GR3.4 | GR7.4 | GR12.3 |
| 10. c | GR2.3 | GR3.4 | GR7.4 | GR12.4 |
| 11. c | GR2.3 | GR3.4 | GR7.5 | GR12.3 |
| 12. c | GR2.3 | GR3.4 | GR7.5 | GR12.4 |
| 13. c | GR2.3 | GR3.5 | GR6/7.3 | GR12.3 |
| 14. c | GR2.3 | GR3.5 | GR6/7.3 | GR12.4 |
| 15. c | GR2.3 | GR3.5 | GR7.4 | GR12.3 |
| 16. c | GR2.3 | GR3.5 | GR7.4 | GR12.4 |
| 17. c | GR2.3 | GR3.5 | GR7.5 | GR12.3 |
| 18. c | GR2.3 | GR3.5 | GR7.5 | GR12.4 |
| 19. c | GR2.4 | GR3.3 | GR6/7.3 | GR12.3 |
| 20. c | GR2.4 | GR3.3 | GR6/7.3 | GR12.4 |
| 21. c | GR2.4 | GR3.3 | GR7.4 | GR12.3 |
| 22. c | GR2.4 | GR3.3 | GR7.4 | GR12.4 |
| 23. c | GR2.4 | GR3.3 | GR7.5 | GR12.3 |
| 24. c | GR2.4 | GR3.3 | GR7.5 | GR12.4 |
| 25. c | GR2.4 | GR3.4 | GR6/7.3 | GR12.3 |
| 26. c | GR2.4 | GR3.4 | GR6/7.3 | GR12.4 |
| 27. c | GR2.4 | GR3.4 | GR7.4 | GR12.3 |
| 28. c | GR2.4 | GR3.4 | GR7.4 | GR12.4 |
| 29. c | GR2.4 | GR3.4 | GR7.5 | GR12.3 |
| 30. c | GR2.4 | GR3.4 | GR7.5 | GR12.4 |
| 31. c | GR2.4 | GR3.5 | GR6/7.3 | GR12.3 |
| 32. c | GR2.4 | GR3.5 | GR6/7.3 | GR12.4 |
| 33. c | GR2.4 | GR3.5 | GR7.4 | GR12.3 |
| 34. c | GR2.4 | GR3.5 | GR7.4 | GR12.4 |
| 35. c | GR2.4 | GR3.5 | GR7.5 | GR12.3 |
| 36. c | GR2.4 | GR3.5 | GR7.5 | GR12.4 |

Also particularly preferred compounds according to the invention are compounds according to formula 1D,

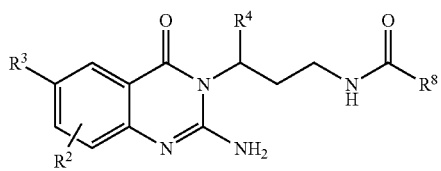

1D wherein
$R^2$, $R^3$, $R^4$, $R^8$, $R^{12}$, $R^{13}$ and $R^{14}$ have the meanings given hereinbefore and pharmaceutically acceptable salts thereof.

More preferred are such compounds of formula 1D wherein $R^2$, $R^3$, $R^4$, $R^8$ and $R^{12}$, are defined as in table 4 below and pharmaceutically acceptable salts thereof.

TABLE 4

| Group No. | $R^2$ | $R^3$ | $R^4$ | $R^8$ | $R^{12}$ |
|---|---|---|---|---|---|
| 1. d | GR2.3 | GR3.3 | GR4.3 | GR8.3 | GR12.3 |
| 2. d | GR2.3 | GR3.3 | GR4.3 | GR8.3 | GR12.4 |
| 3. d | GR2.3 | GR3.3 | GR4.3 | GR8.4 | GR12.3 |
| 4. d | GR2.3 | GR3.3 | GR4.3 | GR8.4 | GR12.4 |
| 5. d | GR2.3 | GR3.3 | GR4.4 | GR8.3 | GR12.3 |
| 6. d | GR2.3 | GR3.3 | GR4.4 | GR8.3 | GR12.4 |
| 7. d | GR2.3 | GR3.3 | GR4.4 | GR8.4 | GR12.3 |
| 8. d | GR2.3 | GR3.3 | GR4.4 | GR8.4 | GR12.4 |
| 9. d | GR2.3 | GR3.3 | GR4.5 | GR8.3 | GR12.3 |
| 10. d | GR2.3 | GR3.3 | GR4.5 | GR8.3 | GR12.4 |
| 11. d | GR2.3 | GR3.3 | GR4.5 | GR8.4 | GR12.3 |
| 12. d | GR2.3 | GR3.3 | GR4.5 | GR8.4 | GR12.4 |
| 13. d | GR2.3 | GR3.4 | GR4.3 | GR8.3 | GR12.3 |
| 14. d | GR2.3 | GR3.4 | GR4.3 | GR8.3 | GR12.4 |
| 15. d | GR2.3 | GR3.4 | GR4.3 | GR8.4 | GR12.3 |
| 16. d | GR2.3 | GR3.4 | GR4.3 | GR8.4 | GR12.4 |
| 17. d | GR2.3 | GR3.4 | GR4.4 | GR8.3 | GR12.3 |
| 18. d | GR2.3 | GR3.4 | GR4.4 | GR8.3 | GR12.4 |
| 19. d | GR2.3 | GR3.4 | GR4.4 | GR8.4 | GR12.3 |
| 20. d | GR2.3 | GR3.4 | GR4.4 | GR8.4 | GR12.4 |
| 21. d | GR2.3 | GR3.4 | GR4.5 | GR8.3 | GR12.3 |
| 22. d | GR2.3 | GR3.4 | GR4.5 | GR8.3 | GR12.4 |
| 23. d | GR2.3 | GR3.4 | GR4.5 | GR8.4 | GR12.3 |
| 24. d | GR2.3 | GR3.4 | GR4.5 | GR8.4 | GR12.4 |
| 25. d | GR2.3 | GR3.5 | GR4.3 | GR8.3 | GR12.3 |
| 26. d | GR2.3 | GR3.5 | GR4.3 | GR8.3 | GR12.4 |
| 27. d | GR2.3 | GR3.5 | GR4.3 | GR8.4 | GR12.3 |
| 28. d | GR2.3 | GR3.5 | GR4.3 | GR8.4 | GR12.4 |
| 29. d | GR2.3 | GR3.5 | GR4.4 | GR8.3 | GR12.3 |
| 30. d | GR2.3 | GR3.5 | GR4.4 | GR8.3 | GR12.4 |
| 31. d | GR2.3 | GR3.5 | GR4.4 | GR8.4 | GR12.3 |
| 32. d | GR2.3 | GR3.5 | GR4.4 | GR8.4 | GR12.4 |
| 33. d | GR2.3 | GR3.5 | GR4.5 | GR8.3 | GR12.3 |
| 34. d | GR2.3 | GR3.5 | GR4.5 | GR8.3 | GR12.4 |
| 35. d | GR2.3 | GR3.5 | GR4.5 | GR8.4 | GR12.3 |
| 36. d | GR2.3 | GR3.5 | GR4.5 | GR8.4 | GR12.4 |
| 37. d | GR2.4 | GR3.3 | GR4.3 | GR8.3 | GR12.3 |
| 38. d | GR2.4 | GR3.3 | GR4.3 | GR8.3 | GR12.4 |
| 39. d | GR2.4 | GR3.3 | GR4.3 | GR8.4 | GR12.3 |
| 40. d | GR2.4 | GR3.3 | GR4.3 | GR8.4 | GR12.4 |
| 41. d | GR2.4 | GR3.3 | GR4.4 | GR8.3 | GR12.3 |
| 42. d | GR2.4 | GR3.3 | GR4.4 | GR8.3 | GR12.4 |
| 43. d | GR2.4 | GR3.3 | GR4.4 | GR8.4 | GR12.3 |
| 44. d | GR2.4 | GR3.3 | GR4.4 | GR8.4 | GR12.4 |
| 45. d | GR2.4 | GR3.3 | GR4.5 | GR8.3 | GR12.3 |
| 46. d | GR2.4 | GR3.3 | GR4.5 | GR8.3 | GR12.4 |
| 47. d | GR2.4 | GR3.3 | GR4.5 | GR8.4 | GR12.3 |
| 48. d | GR2.4 | GR3.3 | GR4.5 | GR8.4 | GR12.4 |
| 49. d | GR2.4 | GR3.4 | GR4.3 | GR8.3 | GR12.3 |
| 50. d | GR2.4 | GR3.4 | GR4.3 | GR8.3 | GR12.4 |
| 51. d | GR2.4 | GR3.4 | GR4.3 | GR8.4 | GR12.3 |
| 52. d | GR2.4 | GR3.4 | GR4.3 | GR8.4 | GR12.4 |
| 53. d | GR2.4 | GR3.4 | GR4.4 | GR8.3 | GR12.3 |
| 54. d | GR2.4 | GR3.4 | GR4.4 | GR8.3 | GR12.4 |
| 55. d | GR2.4 | GR3.4 | GR4.4 | GR8.4 | GR12.3 |
| 56. d | GR2.4 | GR3.4 | GR4.4 | GR8.4 | GR12.4 |
| 57. d | GR2.4 | GR3.4 | GR4.5 | GR8.3 | GR12.3 |
| 58. d | GR2.4 | GR3.4 | GR4.5 | GR8.3 | GR12.4 |
| 59. d | GR2.4 | GR3.4 | GR4.5 | GR8.4 | GR12.3 |
| 60. d | GR2.4 | GR3.4 | GR4.5 | GR8.4 | GR12.4 |
| 61. d | GR2.4 | GR3.5 | GR4.3 | GR8.3 | GR12.3 |
| 62. d | GR2.4 | GR3.5 | GR4.3 | GR8.3 | GR12.4 |
| 63. d | GR2.4 | GR3.5 | GR4.3 | GR8.4 | GR12.3 |
| 64. d | GR2.4 | GR3.5 | GR4.3 | GR8.4 | GR12.4 |
| 65. d | GR2.4 | GR3.5 | GR4.4 | GR8.3 | GR12.3 |
| 66. d | GR2.4 | GR3.5 | GR4.4 | GR8.3 | GR12.4 |
| 67. d | GR2.4 | GR3.5 | GR4.4 | GR8.4 | GR12.3 |
| 68. d | GR2.4 | GR3.5 | GR4.4 | GR8.4 | GR12.4 |
| 69. d | GR2.4 | GR3.5 | GR4.5 | GR8.3 | GR12.3 |
| 70. d | GR2.4 | GR3.5 | GR4.5 | GR8.3 | GR12.4 |
| 71. d | GR2.4 | GR3.5 | GR4.5 | GR8.4 | GR12.3 |
| 72. d | GR2.4 | GR3.5 | GR4.5 | GR8.4 | GR12.4 |

Also particularly preferred compounds according to the invention are compounds according to formula 1E,

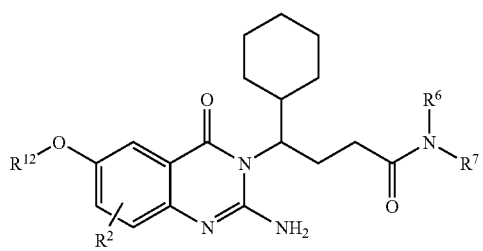

1E wherein
R², R⁶, R⁷, R¹², R¹³ and R¹⁴ have the meanings given hereinbefore and pharmaceutically acceptable salts thereof.

More preferred are such compounds of formula 1E wherein R², R⁶, R⁷ and R¹² are defined as in table 5 below and pharmaceutically acceptable salts thereof.

TABLE 5

| Group No. | $R^2$ | $R^6$ | $R^7$ | $R^{12}$ |
|---|---|---|---|---|
| 1. e | GR2.3 | GR6/7.3 | GR6/7.3 | GR12.3 |
| 2. e | GR2.3 | GR6/7.3 | GR6/7.3 | GR12.4 |
| 3. e | GR2.3 | GR6/7.3 | GR7.4 | GR12.3 |
| 4. e | GR2.3 | GR6/7.3 | GR7.4 | GR12.4 |
| 5. e | GR2.3 | GR6/7.3 | GR7.5 | GR12.3 |
| 6. e | GR2.3 | GR6/7.3 | GR7.5 | GR12.4 |
| 7. e | GR2.3 | GR6.4 | GR6/7.3 | GR12.3 |
| 8. e | GR2.3 | GR6.4 | GR6/7.3 | GR12.4 |
| 9. e | GR2.3 | GR6.4 | GR7.4 | GR12.3 |
| 10. e | GR2.3 | GR6.4 | GR7.4 | GR12.4 |
| 11. e | GR2.3 | GR6.4 | GR7.5 | GR12.3 |
| 12. e | GR2.3 | GR6.4 | GR7.5 | GR12.4 |
| 13. e | GR2.4 | GR6/7.3 | GR6/7.3 | GR12.3 |
| 14. e | GR2.4 | GR6/7.3 | GR6/7.3 | GR12.4 |
| 15. e | GR2.4 | GR6/7.3 | GR7.4 | GR12.3 |
| 16. e | GR2.4 | GR6/7.3 | GR7.4 | GR12.4 |
| 17. e | GR2.4 | GR6/7.3 | GR7.5 | GR12.3 |
| 18. e | GR2.4 | GR6/7.3 | GR7.5 | GR12.4 |
| 19. e | GR2.4 | GR6.4 | GR6/7.3 | GR12.3 |
| 20. e | GR2.4 | GR6.4 | GR6/7.3 | GR12.4 |
| 21. e | GR2.4 | GR6.4 | GR7.4 | GR12.3 |
| 22. e | GR2.4 | GR6.4 | GR7.4 | GR12.4 |
| 23. e | GR2.4 | GR6.4 | GR7.5 | GR12.3 |
| 24. e | GR2.4 | GR6.4 | GR7.5 | GR12.4 |

Also particularly preferred compounds according to the invention are compounds according to formula 1F,

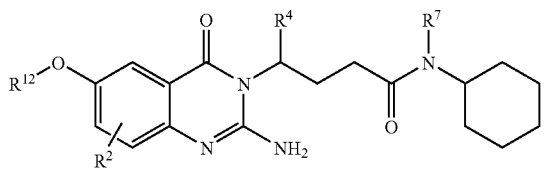

1F wherein
R², R⁴, R⁷, R¹², R¹³ and R¹⁴ have the meanings given hereinbefore and pharmaceutically acceptable salts thereof.

More preferred are such compounds of formula 1F wherein R², R⁴ and R⁷ and R¹² are defined as in table 6 below and pharmaceutically acceptable salts thereof.

TABLE 6

| Group No. | $R^2$ | $R^4$ | $R^7$ | $R^{12}$ |
|---|---|---|---|---|
| 1. f | GR2.3 | GR4.3 | GR6/7.3 | GR12.3 |
| 2. f | GR2.3 | GR4.3 | GR7.4 | GR12.3 |
| 3. f | GR2.3 | GR4.3 | GR7.5 | GR12.3 |
| 4. f | GR2.3 | GR4.4 | GR6/7.3 | GR12.3 |
| 5. f | GR2.3 | GR4.4 | GR7.4 | GR12.3 |
| 6. f | GR2.3 | GR4.4 | GR7.5 | GR12.3 |
| 7. f | GR2.3 | GR4.5 | GR6/7.3 | GR12.3 |
| 8. f | GR2.3 | GR4.5 | GR7.4 | GR12.3 |
| 9. f | GR2.3 | GR4.5 | GR7.5 | GR12.3 |
| 10. f | GR2.4 | GR4.3 | GR6/7.3 | GR12.3 |
| 11. f | GR2.4 | GR4.3 | GR7.4 | GR12.3 |
| 12. f | GR2.4 | GR4.3 | GR7.5 | GR12.3 |
| 13. f | GR2.4 | GR4.4 | GR6/7.3 | GR12.3 |
| 14. f | GR2.4 | GR4.4 | GR7.4 | GR12.3 |
| 15. f | GR2.4 | GR4.4 | GR7.5 | GR12.3 |
| 16. f | GR2.4 | GR4.5 | GR6/7.3 | GR12.3 |
| 17. f | GR2.4 | GR4.5 | GR7.4 | GR12.3 |
| 18. f | GR2.4 | GR4.5 | GR7.5 | GR12.3 |
| 19. f | GR2.3 | GR4.3 | GR6/7.3 | GR12.4 |
| 20. f | GR2.3 | GR4.3 | GR7.4 | GR12.4 |
| 21. f | GR2.3 | GR4.3 | GR7.5 | GR12.4 |
| 22. f | GR2.3 | GR4.4 | GR6/7.3 | GR12.4 |
| 23. f | GR2.3 | GR4.4 | GR7.4 | GR12.4 |
| 24. f | GR2.3 | GR4.4 | GR7.5 | GR12.4 |
| 25. f | GR2.3 | GR4.5 | GR6/7.3 | GR12.4 |
| 26. f | GR2.3 | GR4.5 | GR7.4 | GR12.4 |
| 27. f | GR2.3 | GR4.5 | GR7.5 | GR12.4 |
| 28. f | GR2.4 | GR4.3 | GR6/7.3 | GR12.4 |
| 29. f | GR2.4 | GR4.3 | GR7.4 | GR12.4 |
| 30. f | GR2.4 | GR4.3 | GR7.5 | GR12.4 |
| 31. f | GR2.4 | GR4.4 | GR6/7.3 | GR12.4 |
| 32. f | GR2.4 | GR4.4 | GR7.4 | GR12.4 |
| 33. f | GR2.4 | GR4.4 | GR7.5 | GR12.4 |
| 34. f | GR2.4 | GR4.5 | GR6/7.3 | GR12.4 |
| 35. f | GR2.4 | GR4.5 | GR7.4 | GR12.4 |
| 36. f | GR2.4 | GR4.5 | GR7.5 | GR12.4 |

Also particularly preferred compounds according to the invention are compounds according to formula 1G,

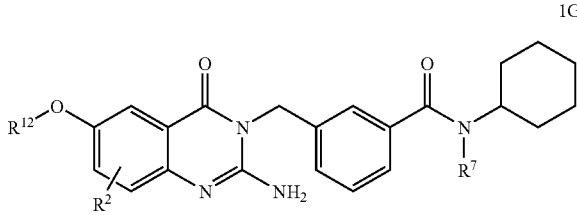

1G wherein
R², R⁷, R¹², R¹³ and R¹⁴ have the meanings given hereinbefore and pharmaceutically acceptable salts thereof.

More preferred are such compounds of formula 1G wherein R², R⁷ and R¹² are defined as in table 7 below and pharmaceutically acceptable salts thereof.

TABLE 7

| Group No. | $R^2$ | $R^7$ | $R^{12}$ |
|---|---|---|---|
| 1. g | GR2.3 | GR6/7.3 | GR12.3 |
| 2. g | GR2.3 | GR6/7.3 | GR12.4 |
| 3. g | GR2.3 | GR7.4 | GR12.3 |
| 4. g | GR2.3 | GR7.4 | GR12.4 |
| 5. g | GR2.3 | GR7.5 | GR12.3 |
| 6. g | GR2.3 | GR7.5 | GR12.4 |
| 7. g | GR2.4 | GR6/7.3 | GR12.3 |
| 8. g | GR2.4 | GR6/7.3 | GR12.4 |

TABLE 7-continued

| Group No. | R² | R⁷ | R¹² |
|---|---|---|---|
| 9. g | GR2.4 | GR7.4 | GR12.3 |
| 10. g | GR2.4 | GR7.4 | GR12.4 |
| 11. g | GR2.4 | GR7.5 | GR12.3 |
| 12. g | GR2.4 | GR7.5 | GR12.4 |

Also particularly preferred compounds according to the invention are compounds according to formula 1H,

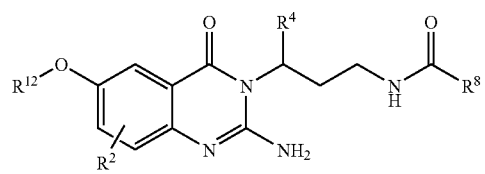

1H wherein $R^2$, $R^4$, $R^8$, $R^{12}$, $R^{13}$ and $R^{14}$ have the meanings given hereinbefore and pharmaceutically acceptable salts thereof.

More preferred are such compounds of formula 1H wherein $R^2$, $R^4$, $R^8$, $R^{12}$, $R^{13}$ and $R^{14}$, are defined as in table 8 below and pharmaceutically acceptable salts thereof.

TABLE 8

| Group No. | R² | R⁴ | R⁸ | R¹² |
|---|---|---|---|---|
| 1. h | GR2.3 | GR4.3 | GR8.3 | GR12.3 |
| 2. h | GR2.3 | GR4.3 | GR8.3 | GR12.4 |
| 3. h | GR2.3 | GR4.3 | GR8.4 | GR12.3 |
| 4. h | GR2.3 | GR4.3 | GR8.4 | GR12.4 |
| 5. h | GR2.3 | GR4.4 | GR8.3 | GR12.3 |
| 6. h | GR2.3 | GR4.4 | GR8.3 | GR12.4 |
| 7. h | GR2.3 | GR4.4 | GR8.4 | GR12.3 |
| 8. h | GR2.3 | GR4.4 | GR8.4 | GR12.4 |
| 9. h | GR2.3 | GR4.5 | GR8.3 | GR12.3 |
| 10. h | GR2.3 | GR4.5 | GR8.3 | GR12.4 |
| 11. h | GR2.3 | GR4.5 | GR8.4 | GR12.3 |
| 12. h | GR2.3 | GR4.5 | GR8.4 | GR12.4 |
| 13. h | GR2.4 | GR4.3 | GR8.3 | GR12.3 |
| 14. h | GR2.4 | GR4.3 | GR8.3 | GR12.4 |
| 15. h | GR2.4 | GR4.3 | GR8.4 | GR12.3 |
| 16. h | GR2.4 | GR4.3 | GR8.4 | GR12.4 |
| 17. h | GR2.4 | GR4.4 | GR8.3 | GR12.3 |
| 18. h | GR2.4 | GR4.4 | GR8.3 | GR12.4 |
| 19. h | GR2.4 | GR4.4 | GR8.4 | GR12.3 |
| 20. h | GR2.4 | GR4.4 | GR8.4 | GR12.4 |
| 21. h | GR2.4 | GR4.5 | GR8.3 | GR12.3 |
| 22. h | GR2.4 | GR4.5 | GR8.3 | GR12.4 |
| 23. h | GR2.4 | GR4.5 | GR8.4 | GR12.3 |
| 24. h | GR2.4 | GR4.5 | GR8.4 | GR12.4 |

Also particularly preferred compounds according to the invention are compounds according to formula 1I,

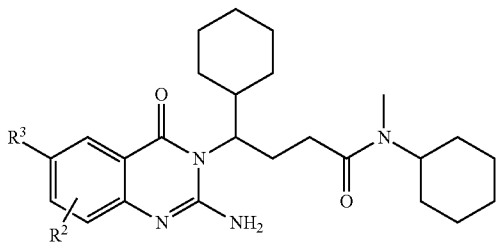

1I wherein $R^2$, $R^3$, $R^{12}$, $R^{13}$ and $R^{14}$ have the meanings given hereinbefore and pharmaceutically acceptable salts thereof.

Most preferred are such compounds of formula 1I wherein $R^2$ is H—, $R^3$ is selected from the group GR3.5 consisting of
Br, phenyl, and phenyl-O—,
wherein the above-mentioned phenyl group may optionally be substituted by one or more
$H_3C$—$CH_2$—O—.

and pharmaceutically acceptable salts thereof.

The compounds herein described may have asymmetric centres. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, —$C_{1-6}$ alkyl means an alkyl group or radical having 1 to 6 carbon atoms. In general, for groups comprising two or more subgroups, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

In general, all tautomeric forms and isomeric forms and mixtures, whether individual geometric isomers or optical isomers or racemic or non-racemic mixtures of isomers, of a chemical structure or compound is intended, unless the specific stereochemistry or isomeric form is specifically indicated in the compound name or structure.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like. (also see Pharmaceutical salts, Birge, S. M. et al., J. Pharm. Sci., (1977), 66, 1-19). As the compounds of the present invention may have both, acid as well as basic groups, those compounds may therefore be present as internal salts too.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

The term halogen denotes an atom selected from among F, Cl, Br and I.

The term $C_{1-n}$-alkyl, wherein n may have a value from 1 to 10, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl etc.

The term $C_{2-n}$-alkenyl, wherein n has a value of 3 to 6, denotes a branched or unbranched hydrocarbon group with 2 to n C atoms and a C=C double bond. Examples of such groups include ethenyl, 1-propenyl, 2-propenyl, iso-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl etc.

The term $C_{2-n}$-alkynyl, wherein n has a value of 3 to 6, denotes a branched or unbranched hydrocarbon group with 2 to n C atoms and a CC triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc.

The term $C_{1-n}$-alkoxy or $C_{1-n}$-alkyloxy denotes a $C_{1-n}$-alkyl-O group, wherein $C_{1-n}$-alkyl is defined as above. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{3-n}$-cycloalkyl denotes a saturated monocyclic group with 3 to n C atoms. Examples of such groups include cyclopropyl, cyclobutyl, cyclopentyl, cyclohexyl, cycloheptyl etc.

The term $C_{3-n}$-cycloalkyloxy denotes a $C_{3-n}$-cycloalkyl-O group wherein $C_{3-n}$-cycloalkyl is defined as above. Examples of such groups include cyclopropyloxy, cyclobutyloxy, cyclopentyloxy, cyclohexyloxy, cycloheptyloxy etc.

The term $C_{3-n}$-cycloalkyl-$C_{1-n}$-alkoxy denotes a $C_{3-n}$-cycloalkyl group wherein $C_{3-n}$-cycloalkyl is defined as above and which is linked to a $C_{1-n}$-alkoxy group through a carbon atom of the $C_{1-n}$-alkoxy group. Examples of such groups include cyclopropylmethyloxy, cyclobutylethyloxy, cyclopentylmethyloxy, cyclohexylmethyloxy, cyclohexylethyloxy etc.

The term $C_{3-n}$-cycloalkenyl denotes a $C_{3-n}$-cycloalkyl group which is defined as above and additionally has at least one C=C double bond, but is not aromatic by nature.

The term heterocyclyl used in this application denotes a saturated five-, six- or seven-membered ring system or a 5-12 membered bicyclic ring system which includes one, two, three or four heteroatoms, selected from N, O and/or S, such as for example a morpholinyl, piperidinyl, piperazinyl, thiomorpholinyl, oxathianyl, dithianyl, dioxanyl, pyrrolidinyl, tetrahydrofuranyl, dioxolanyl, oxathiolanyl, imidazolidinyl, tetrahydropyranyl, pyrrolinyl, tetrahydrothienyl, oxazolidinyl, homopiperazinyl, homopiperidinyl, homomorpholinyl, homothiomorpholinyl, azetidinyl, 1,3-diazacyclohexanyl or pyrazolidinyl group.

The term aryl used in this application denotes a phenyl, biphenyl, indanyl, indenyl, 1,2,3,4-tetrahydronaphthyl or naphthyl group.

The term heteroaryl used in this application denotes a heterocyclic, mono- or bicyclic aromatic ring system which includes in addition to at least one C atom one or more heteroatoms selected from N, O and/or S, wherein the term heteroaryl also includes the partially hydrogenated heterocyclic, aromatic ring systems. Examples of such groups are pyrrolyl, furanyl, thienyl, pyridyl-N-oxide, thiazolyl, imidazolyl, oxazolyl, triazinyl, triazolyl, 1,2,4-oxadiazolyl, 1,3,4-oxadiazoyl, 1,2,5-oxadiazoyl, isothiazolyl, isoxazolyl, 1,2,4-thiadiazolyl, 1,3,4-thiadiazolyl, 1,2,5-thiadiazolyl, pyrazolyl, pyrimidyl, pyridazinyl, pyrazinyl, tetrazolyl, pyridyl, indolyl, isoindoyl, indolizinyl, imidazopyridinyl, imidazo[1,2-a]pyridinyl, pyrrolopyrimidinyl, purinyl, pyridopyrimidinyl, pteridinyl, pyrimidopyrimidinyl, benzofuranyl, benzothienyl, quinolinyl, isoquinolinyl, quinazolinyl, quinoxalinyl, cinnolinyl, phthalazinyl, isobenzofuranyl, isobenzothienyl, thieno[3,2-b]thiophenyl, thieno[3,2-b]pyrrolyl, thieno[2,3-d]imidazolyl, naphthyridinyl, indazolyl, pyrrolopyridinyl, oxazolopyridinyl, benzimidazolyl, benzoxazolyl, benzisoxazolyl, benzothiazolyl, benzoisothiazolyl, benzoxadiazolyl, benzothiadiazolyl, 1,3-benzodioxolyl, 2,3-dihydrobenzofuranyl, 1,3-dihydroisobenzofuranyl, 2,3-dihydrobenzo[1,4]dioxinyl, 3,4-dihydrobenzo[1,4]oxazinyl, benzo[1,4]-oxazinyl, 2,3-dihydroindolyl, 2,3-dihydroisoindolyl, 1,2,3,4-tetrahydroquinolinyl, 1,2,3,4-tetrahydroisoquinolinyl, 2-oxo-2,3-dihydrobenzimidazolyl, 2-oxo-2,3-dihydroindolyl, pyrazolo[1,5-a]pyridinyl, pyrazolo[1,5-a]pyrimidinyl, chromanyl, chromenyl, chromonyl, isochromenyl, isochromanyl, dihydroquinolin-4-onyl, dihydroquinolin-2-onyl, quinolin-4-onyl, isoquinolin-2-onyl, imidazo[1,2-a]pyrazinyl, 1-oxoindanyl, benzoxazol-2-onyl, imidazo[4,5-d]thiazolyl or 6,7-dihydropyrrolizinyl groups.

Preferred heteroaryl groups are furanyl, thienyl, thiazolyl, imidazolyl, isoxazolyl, pyrazolyl, pyridyl, indolyl, benzofuranyl, 1,3-benzodioxolyl, 2,3-dihydrobenzofuranyl and 2,3-dihydrobenzo[1,4]dioxinyl.

The definition pyrazole includes the isomers 1H-, 3H- and 4H-pyrazole. Preferably pyrazolyl denotes 1H-pyrazolyl.

The definition imidazole includes the isomers 1H-, 2H- and 4H-imidazole. A preferred definition of imidazolyl is 1H-imidazolyl.

The definition triazole includes the isomers 1H-, 3H- and 4H-[1,2,4]-triazole as well as 1H-, 2H- and 4H-[1,2,3]-triazole. The definition triazolyl therefore includes 1H-[1,2,4]-triazol-1-, -3- and -5-yl, 3H-[1,2,4]-triazol-3- and -5-yl, 4H-[1,2,4]-triazol-3-, -4- and -5-yl, 1H-[1,2,3]-triazol-1-, -4- and -5-yl, 2H-[1,2,3]-triazol-2-, -4- and -5-yl as well as 4H-[1,2,3]-triazol-4- and -5-yl.

The term tetrazole includes the isomers 1H-, 2H- and 5H-tetrazole. The definition tetrazolyl therefore includes 1H-tetrazol-1- and -5-yl, 2H-tetrazol-2- and -5-yl and 5H-tetrazol-5-yl.

The definition indole includes the isomers 1H- and 3H-indole. The term indolyl preferably denotes 1H-indol-1-yl.

The term isoindole includes the isomers 1H- and 2H-isoindole.

In general, the bond to one of the above-mentioned heterocyclic or heteroaromatic groups may be effected via a C atom or optionally an N atom.

The style of writing used in which in the group

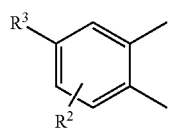

a bond of a substituent $R^2$ is shown towards the centre of the phenyl group denotes, unless stated otherwise, that the substituent $R^2$ may be bound to every free position of the phenyl group carrying an H atom.

The groups and substituents described hereinbefore may be mono- or polysubstituted by fluorine in the manner described. Preferred fluorinated alkyl groups are fluoromethyl, difluoromethyl and trifluoromethyl. Preferred fluorinated alkoxy groups are fluoromethoxy, difluoromethoxy and trifluoromethoxy. Preferred fluorinated alkylsulphinyl and alkylsulphonyl groups are trifluoromethylsulphinyl and trifluoromethylsulphonyl.

The compounds of the instant application are useful for manufacturing a medicament for the prevention and/or treatment of diseases and/or conditions wherein the inhibition of the cleavage of APP (Amyloid Precursor Protein) mediated by R-secretase is of therapeutic benefit.

Preferred is the manufacturing of a medicament for the prevention and/or treatment of Alzheimer's disease (AD) and other diseases which are associated with the abnormal processing of APP or aggregation of Abeta peptide, as well as diseases which can be treated or prevented by the inhibition of β-secretase, particularly AD.

Further preferred is the manufacturing of a medicament for the prevention and/or treatment of e.g. MCI ("mild cognitive impairment"), trisomy 21 (Down's syndrome), cerebral amyloid angiopathy, degenerative dementias, hereditary cerebral haemorrhage with amyloidosis, Dutch type (HCHWA-D), Alzheimer's dementia with Lewy bodies, trauma, stroke, pancreatitis, Inclusion Body Myositis (IBM), and other peripheral amyloidoses, diabetes and arteriosclerosis, most preferably AD.

Other features and advantages of the present invention will become apparent from the following more detailed Examples which illustrate, by way of example, the principles of the invention.

PREPARATION

The compounds according to the invention may be obtained using the methods of synthesis known in principle from starting compounds known to the skilled man (cf. for example: Houben Weyl—Methods of Organic Chemistry, Vol. E22, Synthesis of Peptides and Peptidomimetics, M. Goodman, A. Felix, L. Moroder, C. Toniolo Eds., Georg Thieme Verlag Stuttgart, N.Y.). The skilled man knowing the structure of the compounds according to the invention will be able to synthesise them from known starting materials without any further information. Thus, the compounds may be obtained by the methods of preparation described hereinafter.

Scheme A illustrates as an example the preparation of amines 1, which are intermediates for the synthesis of compounds of formula 1

A known Boc-protected amino-aldehyde or an amino-aldehyde which can be obtained according to literature procedures or in analogy to literature procedures is enlongated by a Wittig reaction or Wittig-Horner-Emmons reaction using a suitable base preferably sodium hydride. The obtained ester is catalytically hydrogenated and subsequently saponified. The resulting acid is coupled with an amine bearing $R^6$, $R^7$ under standard coupling conditions, e.g. using TBTU or EDC (1-Ethyl-3-[3-dimethylaminopropyl]carbodiimide). After this the N-protection group is removed, e.g. the Boc-protection group is cleaved off under acidic conditions, to yield the amine 1.

Scheme A

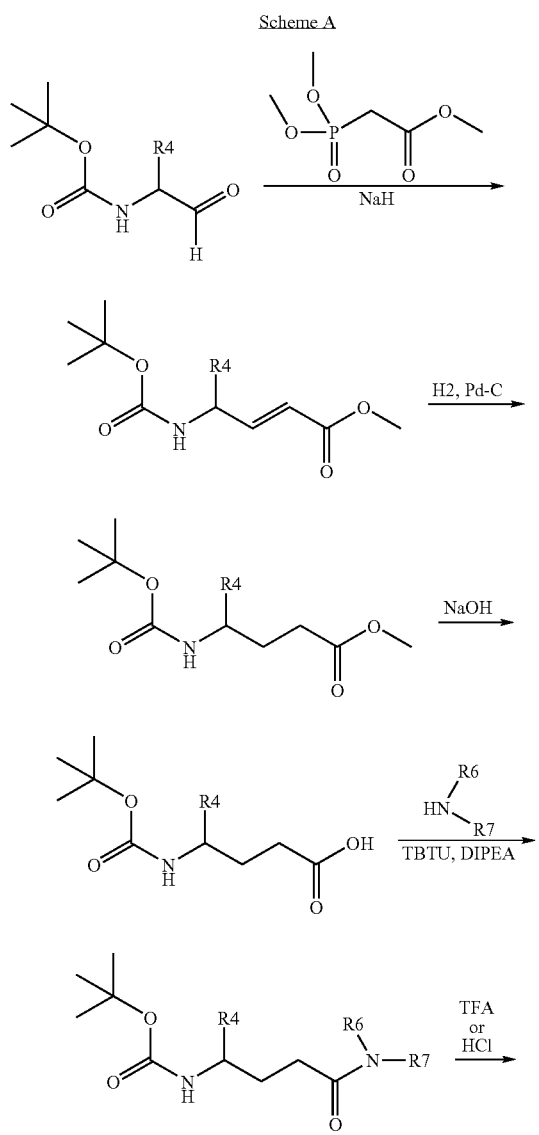

amine 1

Scheme B illustrates as an example the preparation of isothio-cyanates 1, which are intermediates for the synthesis of compounds of formula 1. A known fluorinated nitro-benzoic acid ester or a fluorinated nitro-benzoic acid ester which can be obtained according to literature procedures or in analogy to literature procedures is substituted with a phenol in the presence of a suitable base, e.g. potassium carbonate. After this the nitrogen group is reduced to the amine, e.g. by catalytic hydrogenation. If other functional groups exist in the nitro compound which are labile towards hydrogenation the nitro group is reduced by alternative methods e.g. by the use of tin(II) chloride (stannous chloride). The resulting amines are then reacted with thiophosgene to yield the isothio-cyanates 1.

Scheme B

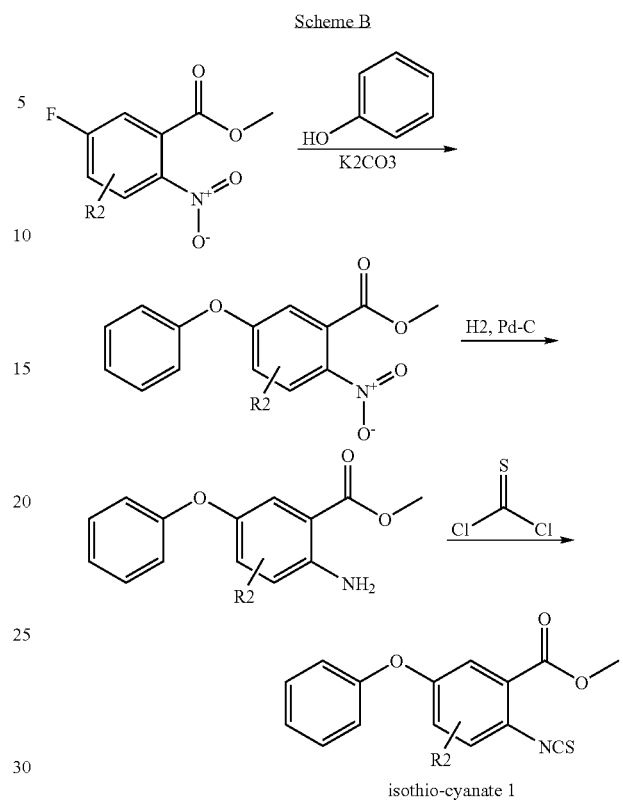

isothio-cyanate 1

Scheme C illustrates as an example the preparation of amines 2, which are intermediates for the synthesis of compounds of formula 1. A known aminomethyl-benzoic acid or a known aminomehtyl-benzoic acid which can be obtained according to literature procedures or in analogy to literature procedures is coupled with an amine bearing $R^6$, $R^7$ under standard coupling conditions, e.g. using TBTU or EDC (1-Ethyl-3-[3-dimethylaminopropyl]carbodiimide). After this the N-protection group is removed, e.g. the Boc-protection group is cleaved off under acidic conditions, to yield the amine 2.

Scheme C

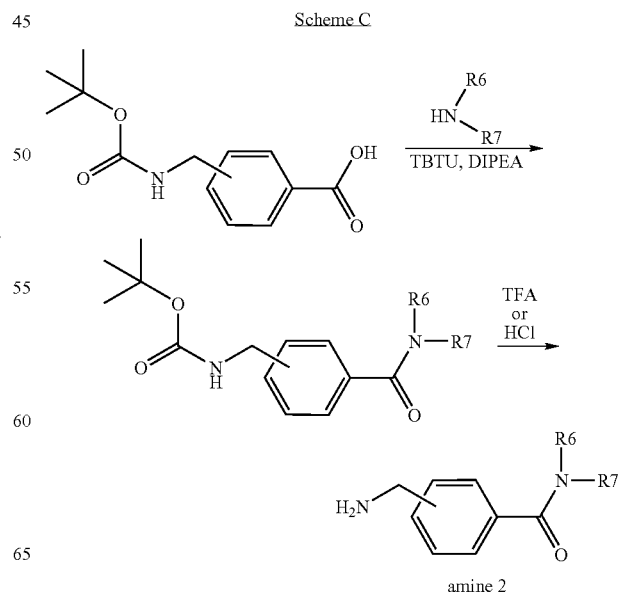

amine 2

Scheme D illustrates as an example the preparation of compounds of formula 1. An isothio-cyanate 1 is reacted with amine 1 or amine 2 in the presence of a suitable base, preferably potassium-tent-butylate. The resulting thioxo-quinazolinone is oxidized at the sulfur and reacted with ammonia to yield the compound of formula 1.

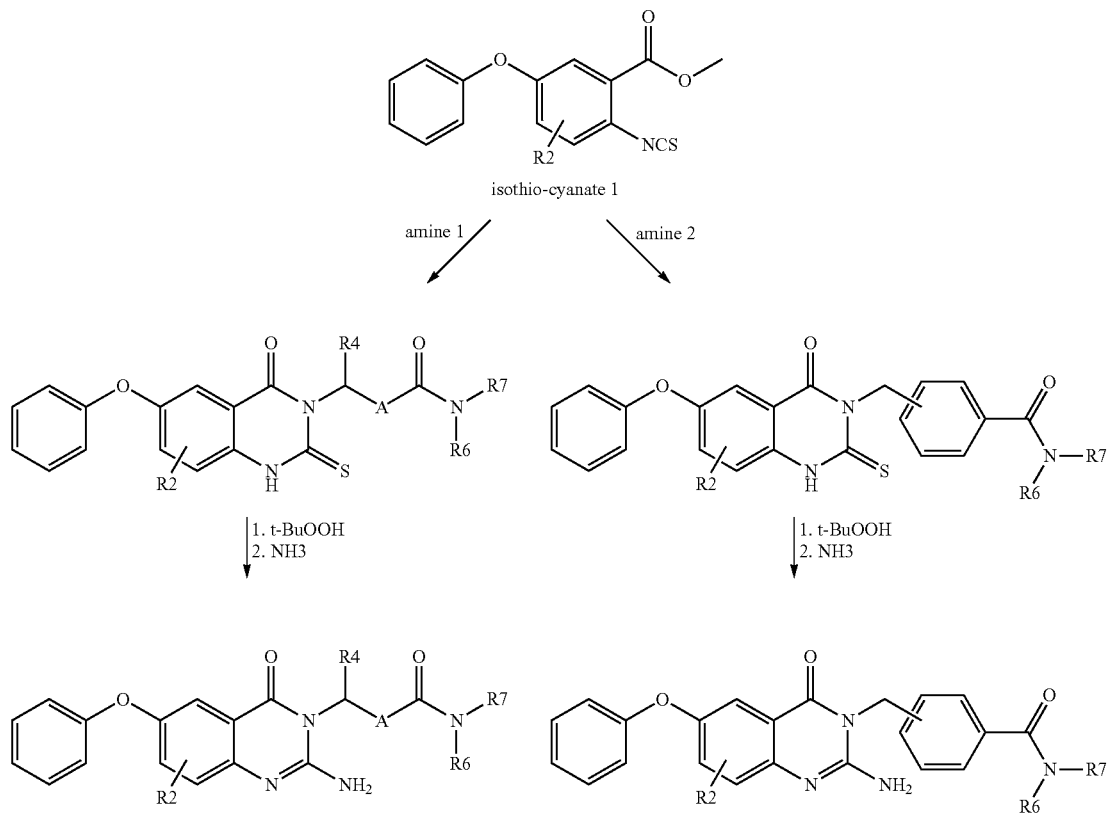

Scheme E illustrates as an example the preparation of compounds of formula 1. An amine 1 (Scheme A) is reacted with thiophosgene in the presence of a suitable base to yield the corresponding isothio-cyanate 2. Addition of carbamic acid tert-butyl ester in the presence of a suitable base, preferably potassium-tert-butylate, yields the intermediate N-Boc-thiourea 1. It is reacted with anthranilic acid ester using 1-ethyl-3-(3-dimethylaminopropyl)carbodiimide hydrochloride (EDC*HCl) to yield the compound of formula 1 either directly or, in cases where the Boc-group is not removed under the reaction conditions, after a separate deprotection step using a suitable acid, preferentially trifluoroacetic acid (TFA).

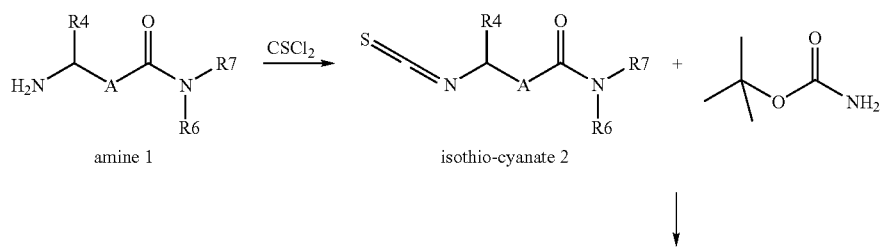

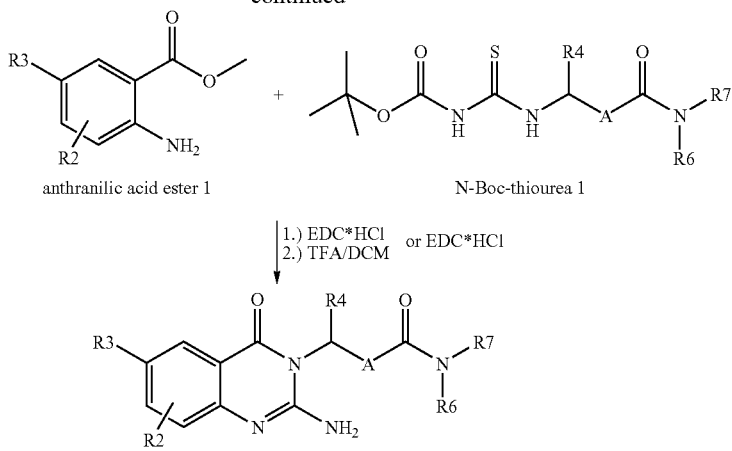

anthranilic acid ester 1      N-Boc-thiourea 1

1.) EDC*HCl  or EDC*HCl
2.) TFA/DCM

As will be appreciated by one of skill in the art, numerous modifications and variations of the present invention are possible in light of the above teachings. It is therefore to be understood that within the scope of the appended claims, the invention may be practiced otherwise than as specifically described herein.

EXAMPLES

In the description of the examples the following abbreviation are used:

| | |
|---|---|
| DIPEA | N-ethyl-diisopropylamine |
| DMF | dimethylformamide |
| dba | 1,5-diphenyl-penta-1,4-dien-3-one |
| EDC*HCl | 1-ethyl-3-(3-dimethylaminopropyl)carbodiimide hydrochloride |
| ESI-MS | electro-spray ionization mass spectrometry |
| h | hours |
| HPLC | high performance liquid chromatography |
| HPLC-MS | high performance liquid chromatography with mass detection |
| min | minutes |
| MPLC | medium pressure liquid chromatography |
| RT | retention time |
| TBTU | O-(benzotriazol-1-yl)-N,N,N',N'-tetramethyluronium tetrafluoroborate |
| TFA | trifluoroacetic acid |
| THF | tetrahydrofurane |
| —* | denotes the binding site of an R-group |

The HPLC Microsorb 1s—data were obtained under the following conditions:

| instrument | Waters Alliance 2695 PDA Detector 2996 Waters Micromass ZQ | column | Varian Microsorb 100 C18 pParticle Size 3 μm lenght 30 mm internal diameter 4.6 mm |
|---|---|---|---|

| gradient time [min] | % water + 0.13% TFA | % acetonitrile | flux [ml/min.] |
|---|---|---|---|
| 0 | 95 | 5 | 3.5 |
| 0.18 | 95 | 5 | 3.5 |
| 2 | 2 | 98 | 3.5 |
| 2.2 | 2 | 98 | 3.5 |
| 2.3 | 95 | 5 | 3.5 |
| 2.5 | 95 | 5 | 3.5 |
| 2.6 | 95 | 5 | 0.5 |
| 6.5 | 95 | 5 | 1.00 |

Example 1

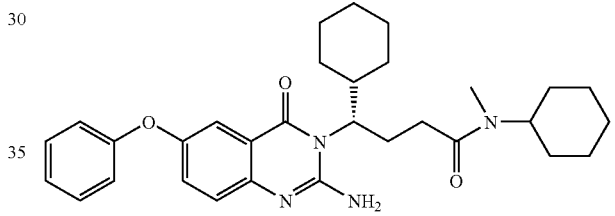

a) Preparation of 1-a:

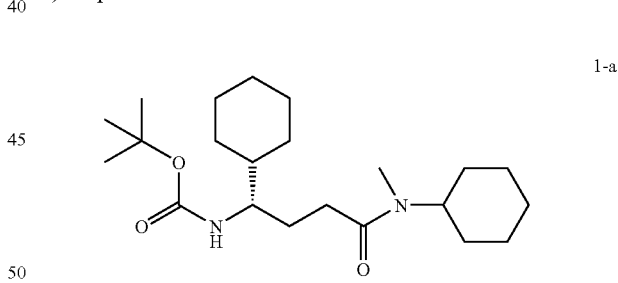

2.12 g (7.44 mmol) (S)-[1-cyclohexyl-3-(cyclohexyl-methyl-carbamoyl)-propyl]-carbamic acid tert-butyl ester (WO 2006/017836) are dissolved in THF and 1.78 ml DIPEA and 2.93 g (7.44 mmol) TBTU is added. The mixture is stirred for 10 min at ambient temperature. 1.07 ml (8.18 mmol) N-Methyl-(cyclohexyl)-amine is added and the mixture is stirred for 14 h at ambient temperature. The mixture is concentrated, dissolved in ethyl acetate and the solution is washed 4 times with a 20% solution of sodium hydrogencarbonate, 1 time with 1 N hydrochloric acid and 1 time with water. The organic phase is dried, concentrated and the residue purified by column chromatography on silica gel (eluent: cyclohexane:ethyl acetate=70:30).

RT (Microsorb 1s)=1.80 min
ESI-MS (M+H)$^+$=381 b) Preparation of 1-b:

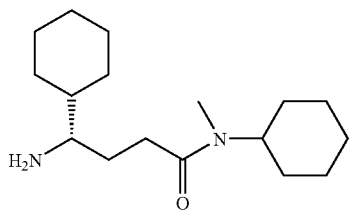

1.29 g (3.38 mol) 1-a are dissolved in 7 ml dioxane and treated with 3.38 ml of a 4 M solution of HCl in dioxane. The mixture is stirred for 2 h at ambient temperature and concentrated. The product is dissolved in sodium hydroxide/methanol and concentrated. The residue is titurated with diethyl ether and collected on a filter plate.

RT (Microsorb 1s)=1.32 min
ESI-MS (M+H)$^+$=281 c) Preparation of 1-c:

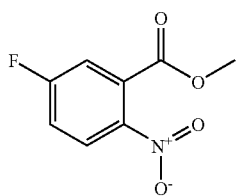

7.0 g (38 mol) 5-fluoro-2-nitro-benzoic acid is dissolved in 30 ml methanol and 10 ml thionyl chloride is added slowly. The solution is heated to reflux for 10 h. The mixture is concentrated and evaporated several times with methanol. 7.1 g of a yellow oil are obtained.

RT (Microsorb 1s)=1.31 min
ESI-MS (M+H)$^+$=200, (M+NH$_4$)$^+$=217 d) Preparation of 1-d:

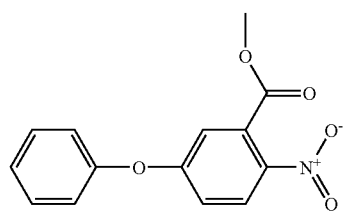

7.11 g (35.7 mmol) 1-c, 3.70 g phenol (39.3 mmol) and 4.93 g (35.7 mmol) potassium carbonate in 30 ml DMF are heated to 120° C. for 1 h. After this the reaction is stirred for 14 h without heating. The mixture is concentrated. Water is added to the residue and the mixture is extracted with ethyl acetate. The combined organic phases are dried, concentrated and the product purified by column chromatography on silica gel (MPLC, eluent: dichloromethane).

yield: 8.59 g
RT (Microsorb 1s)=1.64 min
ESI (M+NH$_4$)$^+$=291 e) Preparation of 1-e:

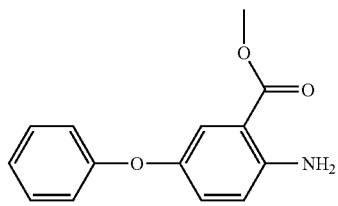

550 mg (2.01 mmol) of compound 1-d are dissolved in 10 ml methanol and hydrogenated 6 h at ambient temperature and 3 bar using 100 mg palladium on activated carbon (10%). The catalyst is removed, the solution filtered over silica gel and concentrated to yield the product as a light yellow resin.

RT (Microsorb 1s)=1.59 min
ESI-MS (M+H)$^+$=244 f) Preparation of 1-f:

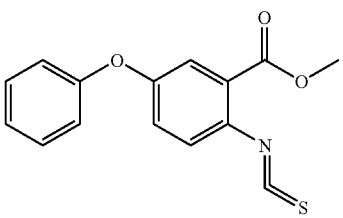

565 mg (2.31 mmol) 1-e are dissolved in 7.5 ml dichloromethane and a saturated solution of sodium hydrogencarbonate is added. While cooling with an ice bath 531 mg (4.62 mmol) of thiophosgene are added. The mixture is stirred for 20 min, allowed to warm to ambient temperature and stirred for 14 h at 37° C. The mixture is treated with saturated solution of sodium hydrogencarbonate and extracted 3 times with dichloromethane. The organic phase is dried and concentrated. 650 mg of a light brown oil is obtained, which was used directly in the next step.

RT (Microsorb 1s)=1.89 min
ESI-MS (M+H)$^+$=286 g) Preparation of 1-g:

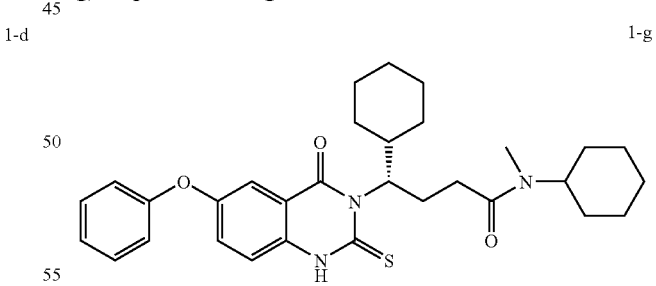

230 mg (0.81 mmol) 1-f and 240 mg (0.86 mmol) 1-b are added to 5 ml DMF and stirred 14 h at 80° C. After this 45 mg (0.40 mmol) potassium-tert-butylate is added and the reaction is stirred for 6 h at 80° C. The solvent is removed, the residue dissolved in dichloromethane, washed 3 times with 0.5 M hydrochloric acid, and the organic phase dried and concentrated. A yellow resin is obtained, which was used as such in the following reaction.

RT (Microsorb 1s)=2.16 min
ESI-MS (M+H)$^+$=534 h) Preparation of 1-h:

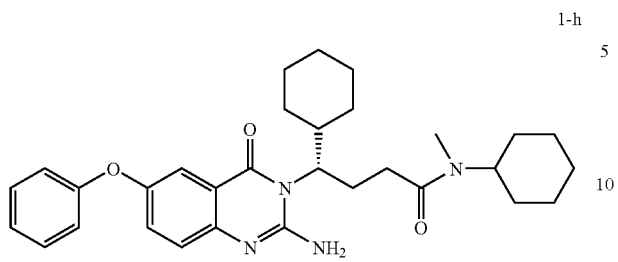

To a solution of 250 mg (0.47 mmol) 1-g in 10 ml isopropyl alcohol are added 3 ml of a 32% solution of ammonia in water. After this 0.76 ml (12.3 mmol) of a 70% solution of tert-butyl hydroperoxide in water is added. The reaction is stirred for 14 h at ambient temperature. An additional 1 ml of the above ammonia solution is added. The mixture is purified without further workup on a preparative HPLC (Gilson; Microsorb C18 Dynamax Compression Modules, 8 μm material, 21.4× 250 mm) and lyophilized. 20.6 mg of a white solid are obtained. It is suspended in 1 M hydrochloric acid and extracted 3 times with dichloromethane. After this the organic phase is dried and concentrated. The product is obtained as a colorless resin.

ESI-MS (M-FH)$^+$=517
RT (Microsorb 1s)=1.89 min

Example 2

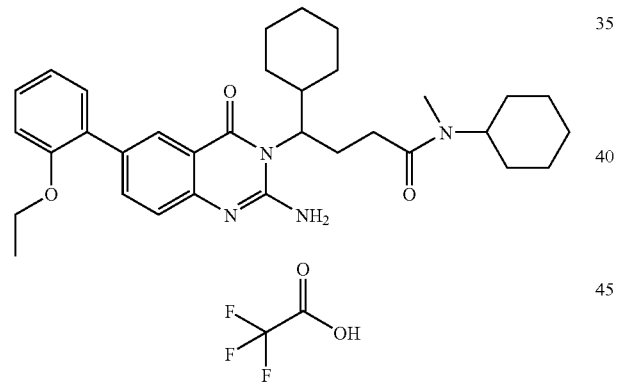

a) Preparation of 2-a:

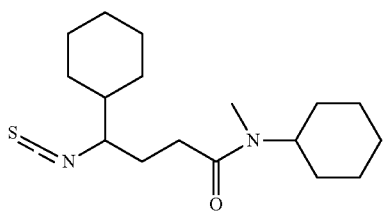

2.20 g (5.58 mmol) 4-Amino-4, N-dicyclohexyl-N-methyl-butyramide (WO 2006/017836) are dissolved in 15 ml dichlormethane and 9.0 ml of a saturated aqueous NaHCO$_3$ solution is added. The reaction mixture is cooled with an ice bath and 480 μl (6.30 mmol) thiophosgene is added and the mixture is stirred 20 min at 0° C. and then warmed to room temperature and stirred 2 h. A saturated aqueous NaHCO$_3$ solution is added and the mixture extracted several times with dichloromethane. The organic layer is dried over MgSO$_4$, filtered and evaporated under reduced pressure. yield: 1.80 g RT (Microsorb 1s)=2.08 min
ESI-MS (M+H)$^+$=323 b) Preparation of 2-b

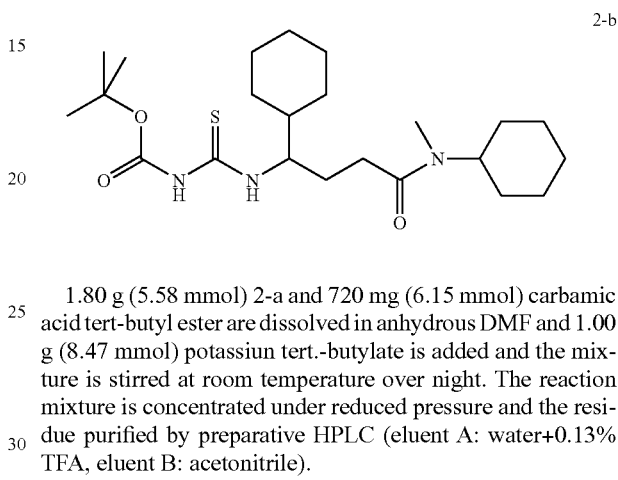

1.80 g (5.58 mmol) 2-a and 720 mg (6.15 mmol) carbamic acid tert-butyl ester are dissolved in anhydrous DMF and 1.00 g (8.47 mmol) potassiun tert.-butylate is added and the mixture is stirred at room temperature over night. The reaction mixture is concentrated under reduced pressure and the residue purified by preparative HPLC (eluent A: water+0.13% TFA, eluent B: acetonitrile).

yield: 1.20 g
RT (Microsorb 1s)=2.01 min
ESI-MS (M+H)$^+$=440 c) Preparation of 2-c

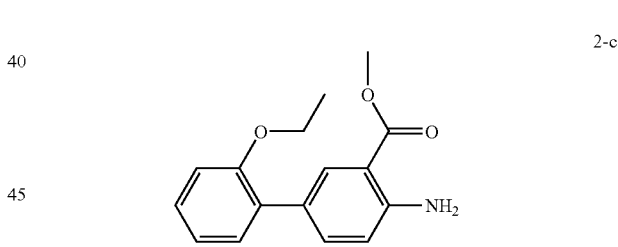

Under an argon atmosphere 200 mg (0.72 mmol) 2-amino-5-iodo-benzoic acid methyl ester is dissolved in 4.0 ml toluene, 156 mg (0.94 mmol) 2-ethoxy-phenylboronic acid, a solution of 475 mg (2.17 mmol) tripotassium phosphate in 0.5 ml water, 53 mg (0.06 mmol) Pd$_2$(dba)$_3$, and 28 mg (0.10 mmol) N-phenyl-2-di-tert.-butylphosphinopyrrole are added. The reaction mixture is heated to 100° C. and stirred over night. After cooling to room temperature the reaction mixture is filtered over celite and the filtrate is evaporated under reduced pressure. The residue is purified by preparative HPLC (eluent A: water+0.13% TFA, eluent B: acetonitrile). The product is dissolved in dichloromethane and extracted with a saturated aqueous solution of Na$_2$CO$_3$. The organic layer is dried and evaporated under reduced pressure.

yield: 40 mg
RT (Microsorb 1s)=1.72 min
ESI-MS (M-FH)$^+$=272 d) Preparation of 2-d

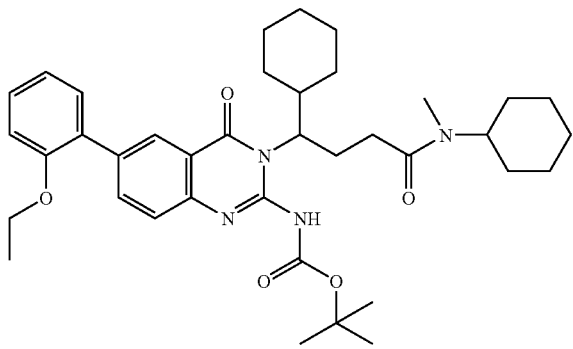

2-d 66 mg (0.15 mmol) 2-b and 40 mg (0.15 mmol) 2-c are dissolved in DMF. Molecular sieve (4A) is added. The suspension is filtered, 90 mg (0.46 mmol) EDC*HCl is added to the filtrate and the reaction mixture is stirred for three weeks under a nitrogen atmosphere. 68 mg (0.61 mmol) Potasssium tert.-butylate is added and the reaction mixture is heated to 80° C. over night. The reaction mixture is acidified with TFA and purified by preparative HPLC (eluent A: water+0.13% TFA, eluent B: acetonitrile).

yield: 20 mg
RT (Microsorb 1s)=2.41 min
ESI-MS (M+H)$^+$=645 e) Preparation of 2-e

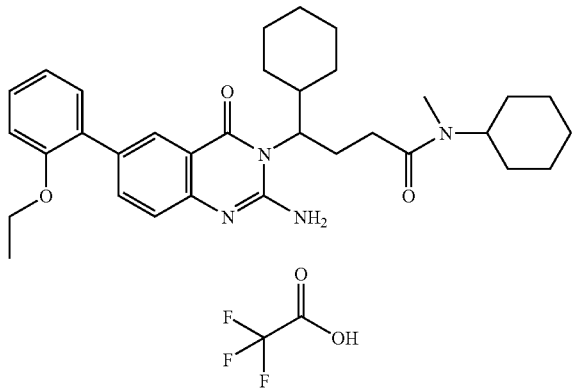

2-e 20 mg (0.15 mmol) 2-d is dissolved in 10 ml dichlormethane and 10 ml TFA (95% in water) is added. The reaction mixture stirred 2 h at room temperature. The solvent is removed under reduced pressure. The residue is disolved in acetonitrile/water 1:1 and lyophilized.

yield: 17 mg
RT (Microsorb 1s)=2.02 min
ESI-MS (M+H)$^+$=545

Example 3

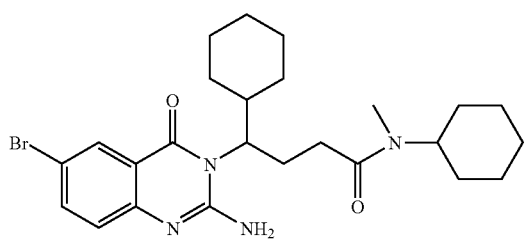

240 mg (0.55 mmol) 2-b and 140 mg (0.61 mmol) 2-amino-5-bromo-benzoic acid methyl ester are dissolved in 2 ml DMF. Molecular sieve (4A) is added. The suspension is filtered, 160 mg (0.83 mmol) EDC.HCl is added to the filtrate and the reaction mixture is stirred for 2 days at room temperature. The reaction mixture is heated to 60° C. and stirred over night. The reaction mixture is evaporated under reduced pressure and puridied by preparative HPLC (Gilson; Waters Xbridge Prep C18, 5 µm material, 100 g, 30×100 mm, eluent A: water+4,5% NH$_4$OH, eluent B: acetonitrile).

yield: 12 mg
RT (Microsorb 1s)=1.96 min
ESI-MS (M+H)$^+$=503/505 (Br)

BIOLOGICAL EXAMPLES

The compounds according to the invention inhibit the proteolysis of the APP protein between the amino acids Met595 and Asp596 (the numbering relates to the APP695 isoform) or the proteolysis of other APP isoforms such as APP751 and APP770 or mutated APP at the corresponding site, which is also referred to as the β-secretase cleavage site. The inhibition of the β-secretase should therefore lead to a reduced production of the β-amyloid peptide (Aβ).

The activity of the β-secretase may be investigated in assays based on different detection techniques. In the test set-up a catalytically active form of β-secretase is incubated with a potential substrate in a suitable buffer. The reduction in the substrate concentration or the increase in the product concentration may be monitored using various technologies as a function of the substrate used: HPLS-MS analysis, fluorescence assays, fluorescence-quenching assays, luminescence assays are a non-representative selection of the various possibilities. Assay systems in which the effectiveness of a compound can be demonstrated are described e.g. in U.S. Pat. No. 5,942,400 and U.S. Pat. No. 5,744,346 and hereinafter. An alternative assay format comprises displacing a known β-secretase ligand with a test substance (US 2003/0125257).

As the substrate, either the APP protein or parts thereof or any amino acid sequence which can be hydrolysed by β-secretase may be used. A selection of such sequences can be found for example in Tomasselli et al. 2003 in J. Neurochem 84: 1006. A peptide sequence of this kind may be coupled to suitable dyes which make it possible to detect proteolysis indirectly.

The enzyme source used may be the total β-secretase enzyme or mutants with a catalytic activity or just parts of the β-secretase which still contain the catalytically active domain. Various forms of β-secretase are known and available and may be used as the enzyme source in a corresponding test set-up. This includes the native enzyme as well as the recombinant or synthetic enzyme. Human β-secretase is known by the name Beta Site APP Cleaving Enzyme (BACE), Asp2 and memapsin 2 and is described e.g. in U.S. Pat. No. 5,744,346 and in Patent Applications WO 98/22597, WO 00/03819, WO 01/23533, and WO 00/17369, as well as in the scientific literature (Hussain et. al., 1999, Mol. Cell. Neurosci. 14: 419-427; Vassar et. al., 1999, Science 286:735-741; Yan et. al., 1999, Nature 402: 533-537; Sinha et. al., 1999, Nature 40: 537-540; and Lin et. al., 2000, PNAS USA 97: 1456-1460). Synthetic forms of the enzyme have also been described (WO 98/22597 and WO 00/17369). β-secretase may be extracted and purified for example from human brain tissue or produced recombinantly in mammalian cell cultures, insect cell cultures, yeasts or bacteria.

To calculate the IC50 value of a substance different amounts of substance are incubated with the β-secretase in an assay. The IC50 value of a compound is defined as the concentration of substance at which a 50% reduction in the detected signal is measured, compared with the mixture without the test compound. Substances are evaluated as inhibiting β-secretase if under these conditions their IC50 value is less than 50 µM, preferably less than 10 µM and particularly preferably less than 1 µM.

In detail, an assay for detecting β-secretase activity may be as follows: The ectodomain of BACE (amino acids 1-454) fused to the recognition sequence for an anti-Myc antibody and a poly-histidine is secreted overnight by HEK293/APP/BACE$_{ect}$ cells in OptiMEM® (Invitrogen). A 10 µl aliquot of this cell culture supernatant is used as the enzyme source. The enzyme is stable over more than 3 months' storage at 4° C. or −20° C. in OptiMEM®. The substrate used is a peptide with the amino acid sequence SEVNLDAEFK, to which the Cy3 fluorophore (Amersham) is coupled N-terminally and the Cy5Q fluorophore (Amersham) is coupled C-terminally. The substrate is dissolved in DMSO in a concentration of 1 mg/ml and used in the experiment in a concentration of 1 µM. The test mixture also contains 20 mM NaOAc, pH 4.4 and a maximum of 1% DMSO. The test is carried out in a 96-well plate in a total volume of 200 µl for 30 minutes at 30° C. The cleaving of the substrate is recorded kinetically in a fluorimeter (ex: 530 nm, em: 590 nm). The assay is started by adding the substrate.

Mixtures without enzyme (i.e. negative control) or without inhibitor (i.e. positive control) are included in each plate as controls.

The compounds listed in the examples have IC$_{50}$ values of less than 15 µM, measured using the test described hereinbefore.

Determination of % Inhibition:

The activity of the positive control (minus the negative control=background) is set to 100% and activity in the presence of test compound is expressed relative to these 100%. Within this setting, an inhibition above 100% might be possible due to the nature of the variation of the positive control within the assay, however, in this case the reported % inhibition had been adjusted to 100%.

In the following, % inhibition data will illustrate that the compounds according to the present invention are suited to inhibit β-secretase and thus provide useful pharmacological properties. The examples are not meant to be limiting.

| Example No. | % Inhibition of β-Secretase at 100 µM |
|---|---|
| 1 | 98 |
| 2 | 81* |
| 3 | 91 |

*due to solubility of the compound a higher inhibition could not be observed

Determination of 1050:

IC50 can be calculated with Graph Pad Prism or other suited software setting the positive control minus the negative control as 100. For calculation of IC50 dilutions of the test compounds (substrates) are to be selected and tested following the aforementioned protocol.

The activity of the β-secretase may also be investigated in cellular systems. As APP is a substrate for β-secretase and Aβ is secreted by the cells after processing of APP by β-secretase has taken place, cellular test systems for detecting β-secretase activity are based on the detection of the amount of Aβ formed over a defined period. A selection of suitable cells includes, but is not restricted to, human embryonic kidney fibroblasts 293 (HEK293), Chinese Hamster Ovary cells (CHO), human H4 neuroglioma cells, human U373 MG astrocytoma glioblastoma cells, murine neuroblastoma N2a cells, which stably or transiently express APP or mutated forms of APP, such as e.g. the Swedish or London or Indiana mutation. The transfection of the cells is carried out e.g. by cloning the cDNA from human APP into an expression vector such as e.g. pcDNA3 (Invitrogen) and adding it to the cells with a transfection reagent such as e.g. lipofectamine (Invitrogen) in accordance with the manufacturer's instructions.

The secretion of Aβ may also be measured from cells without genetic modification with a suitably sensitive Aβ detection assay such as e.g. ELISA or HTRF. Cells which may be used for this may be for example human IMR32 neuroblastoma cells, besides various other cells.

The secretion of Aβ may also be investigated in cells obtained from the brains of embryos or the young of APP transgenic mice, e.g. in those of Hsiao et al 1996 Science 274: 99-102, or from other organisms such as e.g. guinea pigs or rats. Substances are evaluated as inhibiting β-secretase if under these conditions their IC$_{50}$ value is less than 50 µM, preferably less than 10 µM, particularly preferably less than 1 µM.

An example of the method used to carry out a cell assay is described below: U373-MG cells which stably express APP (isoform 751) are cultivated in a culture medium such as DMEM+glucose, sodium pyruvate, glutamine and 10% FCS at 37° C. in a steam-saturated atmosphere with 5% $CO_2$. In order to investigate the β-secretase inhibiting activity of substances the cells are incubated with different concentrations of the compound between 50 µM and 50 µM for 12-24 h. The substance is dissolved in DMSO and diluted for the assay in culture medium such that the DMSO concentration does not exceed 0.5%. The production of Aβ during this period is determined using an ELISA which uses the antibodies 6E10 (Senentek) and SGY3160 (C. Eckman, Mayo Clinic, Jacksonville, Fla., USA) as capturing antibodies which are bound to the microtitre plate and Aβ40 and Aβ42-specific antibodies (Nanotools, Germany), coupled to alkaline phosphatase as detection antibodies. Non-specific binding of proteins to the microtitre plate is prevented by blocking with Block Ace (Serotec) before the addition of the Aβ-containing culture supernatant. The amounts of Aβ contained in the cell supernatant are quantified by adding the substrate for alkaline phosphatase CSPD/Sapphire II (Applied Biosystems) in accordance with the manufacturer's instructions. Possible non-specific effects of the test compound on the vitality of the cell are ruled out by determining this by AlamarBlue (Resazurin) reduction over a period of 60 minutes.

The potency of non-toxic substances is determined by calculating the concentration which results in a 50% reduction in the amount of Aβ secreted by comparison with untreated cells.

In addition, various animal models may be used to investigate the β-secretase activity and/or the APP processing and the release of Aβ. Thus, for example, transgenic animals which express APP and/or β-secretase are used to test the inhibitory activity of compounds of this invention. Corresponding transgenic animals are described e.g. in U.S. Pat. No. 5,877,399, U.S. Pat. No. 5,612,486, U.S. Pat. No. 5,387,742, U.S. Pat. No. 5,720,936, U.S. Pat. No. 5,850,003, U.S. Pat. No. 5,877,015 and U.S. Pat. No. 5,811,633, and in Games et. al., 1995, Nature 373: 523. It is preferable to use animal models which exhibit some of the characteristics of AD pathology. The addition of β-secretase inhibitors according to this invention and subsequent investigation of the pathology of the animals is another alternative for demonstrating the β-secretase inhibition by the compounds. The compounds are administered in such a way that they are able to reach their site of activity in a pharmaceutically effective form and amount.

The Examples that follow are intended to illustrate the invention, without restricting it thereto.

Method of Treatment

The present invention is directed to compounds of general formula 1, which are here shown to be useful in the prevention and/or treatment of a disease and/or condition wherein the inhibition of the cleavage of APP (Amyloid Precursor Protein) mediated by β-secretase is of therapeutic benefit, including but not limited to AD.

Accordingly, the present invention relates to a compound of general formula 1 as a medicament.

Furthermore, the present invention relates to the use of a compound of general formula 1 for the preparation of a medicament for treatment or prevention of a disease and/or condition wherein the inhibition of the cleavage of APP (Amyloid Precursor Protein) mediated by β-secretase is of therapeutic benefit.

Furthermore, the present invention relates to the use of a compound of general formula 1 for the preparation of a medicament for treatment or prevention of Alzheimer's disease, MCI ("mild cognitive impairment"), trisomy 21 (Down's syndrome), cerebral amyloid angiopathy, degenerative dementias, hereditary cerebral haemorrhage with amyloidosis, Dutch type (HCHWA-D), Alzheimer's dementia with Lewy bodies, trauma, stroke, pancreatitis, Inclusion Body Myositis (IBM), and other peripheral amyloidoses, diabetes and arteriosclerosis.

Furthermore, the present invention preferably relates to the use of a compound of general formula 1 for the preparation of a medicament for treatment or prevention of Alzheimer's disease.

In a further aspect of the present invention the present invention relates to methods for the treatment or prevention of above mentioned diseases and conditions, which method comprises the administration of an effective amount of a compound of general formula 1 to a subject.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species.

The subject treated in the methods above is a mammal, male or female, in whom inhibition of the cleavage of APP (Amyloid Precursor Protein) mediated by β-secretase is desired.

The dose range of the compounds of general formula 1 applicable per day is usually from 0.1 to 1000 mg, preferably from 2 to 500 mg, more preferably from 5 to 250 mg, most preferably from 10 to 100 mg. A dosage unit (e.g. a tablet) preferably contains between 2 and 250 mg, particularly preferably between 10 and 100 mg of the compounds according to the invention.

Preferably, the pharmaceutical formulations are administered 1, 2, 3 or 4 times, particularly preferably 1-2 times, most preferably once a day.

The actual pharmaceutically effective amount or therapeutic dosage will of course depend on factors known by those skilled in the art such as age and weight of the patient, route of administration and severity of disease.

In another aspect the present invention is directed to the use of the compounds of general formula 1 in the preparation and execution of screening assays for compounds that modulate the activity of β-secretase. Furthermore, the compounds of this invention are useful in establishing or determining the binding site of other compounds to β-secretase, e.g., by competitive inhibition or as a reference in an assay to compare its known activity to a compound with an unknown activity. When developing new assays or protocols, compounds according to the present invention could be used to test their effectiveness.

Specifically, such compounds may be provided in a commercial kit, for example, for use in pharmaceutical research involving the aforementioned diseases. The compounds of the instant invention are also useful for the evaluation of putative specific inhibitors of β-secretase.

Combinations

The compounds of general formula 1 may be used on their own or combined with other active substances of formula 1 according to the invention. The compounds of general formula 1 may optionally also be combined with other pharmacologically active substances. These include, for example beta-secretase inhibitors; gamma-secretase inhibitors; amyloid aggregation inhibitors such as e.g. alzhemed; directly or indirectly acting neuroprotective substances; anti-oxidants, such as e.g. vitamin E or ginkolide; anti-inflammatory substances, such as e.g. Cox inhibitors, NSAIDs additionally or exclusively having Aβ lowering properties; HMG-CoA reductase inhibitors (statins); acetylcholinesterase inhibitors, such as donepezil, rivastigmine, tacrine, galantamine; NMDA receptor antagonists such as e.g. memantine; AMPA agonists; substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE-IV and PDE-IX inhibitors, $GABA_A$ inverse agonists, nicotinic agonists, histamine H3 antagonists, 5 HAT-4 agonists or partial agonists, 5HT-6 antagonists, a2-adrenoreceptor antagonists, muscarinic M1 agonists, muscarinic M2 antagonists, metabotropic glutamate-receptor 5 positive modulators, and other substances that modulate receptors or enzymes in a manner such that the efficacy and/or safety of the compounds according to the invention is increased and/or unwanted side effects are reduced.

This invention further relates to pharmaceutical compositions containing one or more, preferably one active substance, which is selected from the compounds according to the invention and/or the corresponding salts, as well as one or more, preferably one active substance selected from among alzhemed, vitamin E, ginkolide, donepezil, rivastigmine, tacrine, galantamine, memantine, ibutamoren mesylate, capromorelin, minocyclin and/or rifampicin, optionally together with one or more inert carriers and/or diluents.

The compounds according to the invention may also be used in combination with immunotherapies such as e.g. active immunisation with Abeta or parts thereof or passive immunisation with humanised anti-Abeta antibodies for the treatment of the above-mentioned diseases and conditions.

The combinations according to the present invention may be provided simultaneously in one and the same dosage form, i.e. in form of a combination preparation, for example the two components may be incorporated in one tablet, e.g. in different layers of said tablet. The combination may be also provided separately, in form of a free combination, i.e the compounds of the present invention are provided in one dosage form and one or more of the above mentioned combination partners is provided in another dosage form. These two dosage forms may be equal dosage forms, for example a co-administration of two tablets, one containing a therapeutically effective amount of the compound of the present invention and one containing a therapeutically effective amount of the above mentioned combination partner. It is also possible to combine different administration forms, if desired. Any type of suitable administration forms may be provided.

The compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

The dosage or administration forms are not limited, in the frame of the present invention any suitable dosage form may be used. Exemplarily the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present.

Depending from the administration route and dosage form the ingredients are selected accordingly.

The dosage for the above-mentioned combination partners is expediently 1/5 of the normally recommended lowest dose up to 1/1 of the normally recommended dose.

The dosage forms are administered to the patient 1, 2, 3, or 4 times daily. It is preferred that the compounds of the invention be administered either three or fewer times, more preferably once or twice daily.

Therefore, in another aspect the invention relates to the use of a combination of compounds of general formula 1, or a pharmaceutically acceptable salt thereof, and of one or more, preferably one active ingredient described above as combination partners, for the manufacture of a medicament for the treatment and/or prevention of diseases and/or conditions which can be influenced by the inhibition of R-secretase.

In another aspect, the invention relates to the use of a compound of general formula 1, or a pharmaceutically acceptable salt thereof, for the manufacture of a medicament for the treatment and/or prevention of diseases or conditions which can be influenced by the inhibition of R-secretase, in combination with one or more, preferably one active ingredient described above as combination partners.

Pharmaceutical Forms

The compounds of formula 1 are administered to a mammal in a therapeutically effective amount. By "therapeutically effective amount" it is meant an amount of a compound of formula 1 that, when administered alone or in combination with an additional therapeutic agent to a mammal, is effective to prevent or ameliorate diseases, wherein the activity of a β-secretase is involved, or the progression of this disease.

The compounds according to the invention may be administered by oral, parenteral (intravenous, intramuscular etc.), intranasal, sublingual, inhalative, intrathecal, topical or rectal route. Suitable preparations for administering the compounds of formula 1 include for example patches, tablets, capsules, pills, pellets, dragees, powders, troches, suppositories, liquid preparations such as solutions, suspensions, emulsions, drops, syrups, elixirs, or gaseous preparations such as aerosols, sprays and the like. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatin and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

The dosage of the compounds according to the invention is naturally highly dependent on the method of administration and the complaint which is being treated. When administered by inhalation the compounds of formula 1 are characterised by a high potency even at doses in the μg range. The compounds of formula 1 may also be used effectively above the μg range. The dosage may then be in the gram range, for example.

In another aspect the present invention relates to the abovementioned pharmaceutical formulations as such which are characterised in that they contain a compound of formula 1.

The following examples of formulations illustrate the present invention without restricting its scope:

EXAMPLES OF PHARMACEUTICAL FORMULATIONS

Some examples of formulations will now be described, wherein the term "active substance" denotes one or more compounds according to the invention including the salts thereof. In the case of one of the aforementioned combinations with one or more other active substances the term "active substance" also includes the additional active substances.

Example A

Tablets Containing 100 mg of Active Substance
Composition:

| 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| Weight of tablet: | 220 mg |
|---|---|
| Diameter: | 10 mm, biplanar, facetted on both sides and notched on one side. |

Example B

Tablets Containing 150 mg of Active Substance Composition:

| 1 tablet contains: | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| Weight of tablet: | 300 mg |
|---|---|
| diameter: | 10 mm, flat |

Example C

Hard Gelatine Capsules Containing 150 Ring of Active Substance

| 1 capsule contains: | |
|---|---|
| active substance | 150.0 mg |
| corn starch (dried) | approx. 80.0 mg |
| lactose (powdered) | approx. 87.0 mg |
| magnesium stearate | 3.0 mg |
| | approx. 320.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

Example D

Suppositories Containing 150 MCI of Active Substance

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example E

Ampoules Containing 10 mg Active Substance
Composition:

| active substance | 10.0 mg |
|---|---|
| 0.01N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

Example F

Ampoules Containing 50 mg of Active Substance
Composition:

| active substance | 50.0 mg |
|---|---|
| 0.01N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

The invention claimed is:

1. A compound of general formula 1

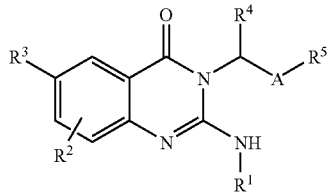

wherein
A is selected from the group consisting of
  a $C_1$-$C_3$-alkylene bridge, aryl-, heteroaryl- and heterocyclyl-,
  wherein the above-mentioned members of the group may optionally be substituted independently of one another by one or more substituents selected from the group consisting of
  fluorine, chlorine, bromine, HO—, NC—, $O_2N$—, $F_3C$—, $HF_2C$—, $FH_2C$—, $F_3C$—$CH_2$—, $R^{14}$—O—$C_{1-6}$-alkyl-, $C_{1-6}$-alkyl-, $C_{1-6}$-alkyl-O—, $F_3C$—O—, $HF_2C$—O—, $FH_2C$—O—, $(R^{13})_2N$—, $(R^{13})_2N$—$C_{1-3}$-alkyl-, and $(R^{13})_2N$—CO—,
$R^1$ is selected from the group consisting of
  H—, HO—, methyl-, ethyl-, $F_3C$—, $F_3C$—$CH_2$—, $H_3C$—O—, $H_3C$—$CH_2$—O—, $H_3C$—C(O)—, $(CH_3)_3C$—O—C(O)— and HC(O)—,
$R^2$ is selected from the group consisting of
  H—, fluorine, chlorine, bromine, HO—, NC—, $O_2N$—, $F_3C$—, $HF_2C$—, $FH_2C$—, $F_3C$—$CH_2$—, $F_3C$—O—, $HF_2C$—O—, $FH_2C$—O—, $C_{1-6}$-alkyl-, $C_{1-6}$-alkyl-S—, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, $R^{14}$—O—, $R^{14}$—O—$C_{1-3}$-alkyl-, $(R^{13})_2N$—, $(R^{13})_2N$—CO—, $R^{13}$—CO—$(R^{13})_2N$—CO—$(R^{13})N$—, $R^{13}$—$SO_2$—$(R^{13})N$—, $(R^{13})_2N$—$SO_2$— and $R^{13}$—$SO_2$—,
  wherein the above-mentioned members of the group may optionally be substituted independently of one another by one or more substituents selected from the group consisting of
  fluorine, chlorine, bromine, HO—, NC—, $O_2N$—, $F_3C$—, $HF_2C$—, $FH_2C$—, HO—$C_{1-6}$-alkyl-, $C_{1-6}$-alkyl-, $C_{1-6}$-alkyl-O—, $(R^{13})_2N$—, $(R^{13})_2N$—$C_{1-3}$-alkyl-, and $(R^{13})_2N$—CO—,
$R^3$ is selected from the group consisting of
  H—, fluorine, chlorine, bromine, HO—, NC—, $F_3C$—, $HF_2C$—, $FH_2C$—, $F_3C$—$CH_2$—, $F_3C$—O—, $HF_2C$—O—, $FH_2C$—O—, $C_{1-6}$-alkyl-, $C_{1-6}$-alkyl-S—, $C_2$-$C_6$-alkenyl, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, $R^{12}$—O—, $R^{12}$—O—$C_{1-3}$-alkyl-, $R^{12}$—S—, $R^{12}$—CO—, $(R^{13})_2N$—, $(R^{13})_2N$—CO—, $R^{13}$—CO—$(R^{13})N$—, $(R^{13})_2N$—CO—$(R^{13})N$—, $R^{13}$—$SO_2$—$(R^{13})N$—, $(R^{13})_2N$—$SO_2$— and $R^{13}$—$SO_2$—,
  wherein the above-mentioned members of the group may optionally be substituted independently of one another by one or more substituents selected from the group consisting of
  fluorine, chlorine, bromine, HO—, NC—, $O_2N$—, $F_3C$—, $HF_2C$—, $FH_2C$—, $F_3C$—$CH_2$—, $R^{14}$—O—, $R^{14}$—O—$C_{1-6}$-alkyl-, $C_{1-6}$-alkyl-, $(R^{13})_2N$—, $(R^{13})_2N$—$C_{1-3}$-alkyl-, and $(R^{13})_2N$—CO—,
$R^4$ is selected from the group consisting of
  H—, fluorine, NC—, $F_3C$—, $HF_2C$—, $FH_2C$—, $F_3C$—$CH_2$—, $C_{1-6}$-alkyl-, $C_2$-$C_6$-alkenyl, $C_{1-6}$-alkyl-S—, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, $R^{14}$—O—, and $R^{14}$—O—$C_{1-3}$-alkyl-,
  wherein the above-mentioned members of the group may optionally be substituted independently of one another by one or more substituents selected from the group consisting of
  fluorine, chlorine, bromine, HO—, NC—, $O_2N$—, $F_3C$—, $HF_2C$—, $FH_2C$—, $F_3C$—$CH_2$—, HO—$C_{1-6}$-alkyl-, $C_{1-6}$-alkyl-, $C_{1-6}$-alkyl-O—, $(R^{13})_2N$—, $(R^{13})_2N$—$C_{1-3}$-alkyl-, and $(R^{13})_2N$—CO—,
$R^5$ is selected from the group consisting of
  $R^6R^7N$—CO—, $R^8$—CO—$(R^9)N$—, and $R^{10}R^{11}N$—CO—$(R^9)N$—,
$R^6$, $R^7$, $R^8$, $R^9$, $R^{10}$, and $R^{11}$
are selected from the group consisting of
  H—, $F_3C$—, $HF_2C$—, $FH_2C$—, $F_3C$—$CH_2$—, $C_{1-6}$-alkyl-, $C_2$-$C_6$-alkenyl, $C_{1-6}$-alkyl-S—$C_{1-3}$alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, and $R^{14}$—O—$C_{1-3}$-alkyl-,
  wherein, if $R^6$ and $R^7$ or $R^{10}$ and $R^{11}$ are $C_{1-6}$-alkyl groups, those two $C_{1-6}$-alkyl groups bound to the same nitrogen atom of $R^5$ may be joined together forming, together with the nitrogen atom to which they are bound, a 3 to 7 membered heterocyclic ring, and wherein one of the —$CH_2$-groups of the heterocyclic ring formed by the $R^6$ and $R^7$ or $R^{10}$ and $R^{11}$ $C_{1-6}$-alkyl groups and the nitrogen atom of $R^5$ may be replaced by —O—, —S—, N—H, —N($C_{3-6}$-cycloalkyl)-, —N($C_{3-6}$-cycloalkyl-$C_{1-4}$-alkyl)- or —N($C_{1-4}$-alkyl)- and wherein the above-mentioned members of the group including the heterocyclic ring formed by the $R^6$ and $R^7$ or $R^{10}$ and $R^{11}$ $C_{1-6}$-alkyl groups and the nitrogen atom of $R^5$ may optionally be substituted independently of one another by one or more substituents selected from group consisting of fluorine, chlorine, bromine, HO—, NC—, $O_2N$—, $F_3C$—, $HF_2C$—, $FH_2C$—, HO—$C_{1-6}$-alkyl-, $C_{1-6}$-alkyl-, $C_{1-6}$-alkyl-O—, aryl-, $(R^{13})_2N$—, $(R^{13})_2N$—$C_{1-3}$-alkyl-, and $(R^{13})_2N$—CO— wherein the above-mentioned aryl of group may optionally be substituted independently of one another by one or more substituents selected from group consisting of fluorine, chlorine, bromine, NC—, $F_3C$—, $HF_2C$—, $FH_2C$—, $F_3C$—$CH_2$—, HO—$C_{1-6}$-alkyl-, $C_{1-6}$-alkyl-, and $C_{1-6}$-alkyl-O—, $R^{12}$ is selected from the group consisting of
$F_3C$—, $HF_2C$—, $FH_2C$—, $F_3C$—$CH_2$—, $C_{1-6}$-alkyl-, $C_{3-6}$-alkenyl-, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, and heteroaryl-$C_{1-6}$-alkyl-, wherein the above-mentioned members of the group may optionally be substituted independently of one another by one or more substituents selected from the group consisting of fluorine, chlorine, bromine, $R^{14}$—O—, NC—, $O_2N$—, $F_3C$—, $HF_2C$—, $FH_2C$—, $F_3C$—$CH_2$—, K O—$C_{1-6}$-alkyl-, $C_{1-6}$-alkyl-, $(R^{13})_2N$—, $(R^{13})_2N$—$C_{1-3}$-alkyl-, and $(R^{13})_2N$—CO—, $R^{13}$ is selected from the group consisting of
H—, $F_3C$—$CH_2$—, $C_{1-6}$-alkyl-, $C_{2-6}$-alkenyl-, $C_{3-7}$-cycloalkyl-, $C_{3-7}$-cycloalkyl-$C_{1-3}$-alkyl-, aryl-, aryl-$C_{1-3}$-alkyl-, heterocyclyl-, heterocyclyl-$C_{1-3}$-alkyl-, heteroaryl-, and heteroaryl-$C_{1-3}$-alkyl-, wherein two $C_{1-6}$-alkyl groups bound to the same nitrogen atom may be joined together forming, together with the nitrogen atom to which they are bound, a 3 to 7 membered heterocyclic ring, and wherein one of the —$CH_2$-groups of the heterocyclic ring formed may be replaced by —O—, —S—, N—H, —N($C_{3-6}$-cycloalkyl)-, —N($C_{3-6}$-cycloalkyl-$C_{1-4}$-alkyl)- or —N($C_{1-4}$-alkyl)- and wherein the above-mentioned members of the group including the heterocyclic ring formed may optionally be substituted independently of one another by one or more substituents selected from the group consisting of fluorine, chlorine, bromine, HO—, NC—, $O_2N$—, $F_3C$—, $HF_2C$—, $FH_2C$—, $F_3C$—$CH_2$—, HO—$C_{1-6}$-alkyl-, $C_{1-6}$-alkyl-, and $C_{1-6}$-alkyl-O—, $R^{14}$ is selected from the group consisting of
H—, $F_3C$—, $HF_2C$—, $FH_2C$—, $F_3C$—$CH_2$—, $C_{1-6}$-alkyl-, $C_{2-6}$-alkenyl-, $C_{3-7}$-cycloalkyl-, $C_{3-7}$-cycloalkyl-$C_{1-3}$-alkyl-, aryl-, aryl-$C_{1-3}$-alkyl-, heterocyclyl-, heterocyclyl-$C_{1-3}$-alkyl-, heteroaryl- and heteroaryl-$C_{1-3}$-alkyl-, wherein the above-mentioned members of the group may optionally be substituted independently of one another by one or more substituents selected from the group consisting of fluorine, chlorine, bromine, HO—, NC—, $O_2N$—, $F_3C$—, $HF_2C$—, $FH_2C$—, $F_3C$—$CH_2$—, HO—$C_{1-6}$-alkyl-, $C_{1-6}$-alkyl-, and $C_{1-6}$-alkyl-O—, or a pharmaceutically acceptable salt thereof.

2. The compound according to claim 1, characterised in that

A is selected from the group consisting of
—CH2—, —CH2—CH2—, —CH2—CH2—CH2—, aryl-, and heteroaryl-, wherein the above-mentioned members of the group may optionally be substituted independently of one another by one or more substituents selected from the group consisting of fluorine, chlorine, bromine, NC—, $F_3C$—, $HF_2C$—, $FH_2C$—, $F_3C$—$CH_2$—, $F_3C$—O—, $HF_2C$—O—, $FH_2C$—O—, $H_3C$—O—$C_{1-6}$-alkyl-, HO—$C_{1-6}$-alkyl-, $C_{1-6}$-alkyl-, and $C_{1-6}$-alkyl-O—.

3. The compound according to claim 1, characterised in that

A is selected from the group consisting of
—CH2—CH2—, —CH2—CH2—CH2—, phenyl-, and pyridyl-, wherein the above-mentioned members of the group may optionally be substituted independently of one another by one or more substituents selected from the group consisting of fluorine, chlorine, NC—, $F_3C$—, $HF_2C$—, $FH_2C$—, $F_3C$—$CH_2$—, $F_3C$—O—, $HF_2C$—O—, $FH_2C$—O', $H_3C$—, and $H_3C$—O—.

4. The compound according to claim 1, characterised in that $R^1$ is H—.

5. The compound according to claim 1, characterised in that $R^2$ is selected from the group consisting of
H—, fluorine, chlorine, bromine, NC—, $F_3C$—, $HF_2C$—, $FH_2C$—, $F_3C$—$CH_2$—, $C_{1-6}$-alkyl-, $C_{1-6}$-alkyl-S—, $C_{3-7}$-cycloalkyl-, $C_{3-7}$-cycloalkyl-$C_{1-6}$-alkyl-, and $R^{14}$—O—.

6. The compound according to claim 1, characterised in that $R^3$ is selected from the group consisting of
fluorine, chlorine, bromine, NC—, $F_3C$—, HFC—, $FH_2C$—, $F_3C$—$CH_2$—, $C_{1-6}$-alkyl-, $C_{1-6}$-alkyl-S—, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, $R^{12}$—O—, $R^{12}$—O—$C_{1-3}$-alkyl-, and $R^{12}$—CO—, wherein the above-mentioned members of the group may optionally be substituted independently of one another by one or more substituents selected from the group consisting of fluorine, chlorine, bromine, HO—, NC—, $F_3C$—, $HF_2C$—, $FH_2C$—, $F_3C$—$CH_2$—, HO—$C_{1-6}$-alkyl-, $C_{1-3}$-alkyl-, $C_{1-6}$-alkyl-O—, and $(R^{13})_2N$—CO—.

7. The compound according to claim 1, characterised in that $R^4$ is selected from the group consisting of
H—, $F_3C$—, $HF_2C$—, $FH_2C$—, $F_3C$—$CH_2$—, $C_{1-6}$-alkyl-, $C_{1-6}$-alkyl-S—$C_{1-3}$-alkyl-, $C_{3-7}$-cycloalkyl-, $C_{3-7}$-cycloalkyl-$C_{1-3}$-alkyl-, aryl-, aryl-$C_{1-6}$-alkyl-, heterocyclyl-, heterocyclyl-$C_{1-3}$-alkyl-, heteroaryl-, heteroaryl-$C_{1-3}$-alkyl-, and $R^{14}$—O—$C_{1-3}$-alkyl-, wherein the above-mentioned members of the group may optionally be substituted independently of one another by one or more substituents selected from the group consisting of fluorine, chlorine, bromine, HO—, NC—, $F_3C$—, HFC—, $FH_2C$—, $F_3C$—$CH_2$—, HO—$C_{1-6}$-alkyl-, $C_{1-6}$-alkyl-, and $C_{1-6}$-alkyl-O—.

8. The compound according to claim 1, characterised in that
$R^5$ is selected from the group consisting of
$R^6R^7N$—CO—.

9. The compound according to claim 1, characterised in that
$R^6$, $R^7$, $R^8$, $R^9$, $R^{10}$ and $R^{11}$
are selected from the group consisting of
H—, $F_3C$—, $HF_2C$—, $FH_2C$—, $F_3C$—$CH_2$—, $C_{1-6}$-alkyl-, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, and $R^{14}$—O—$C_{1-3}$-alkyl-,
wherein, if $R^6$ and $R^7$ or $R^{10}$ and $R^{11}$ are $C_{1-6}$-alkyl groups, those two $C_{1-6}$-alkyl groups bound to the same nitrogen atom of $R^5$ may be joined together forming, together with the nitrogen atom to which they are bound, a 3 to 7 membered heterocyclic ring, and
wherein the above-mentioned members of the group including the heterocyclic ring formed by the $R^6$ and $R^7$ or $R^{10}$ and $R^{11}C_{1-6}$-alkyl groups and the nitrogen atom of $R^5$ may optionally be substituted independently of one another by one or more substituents selected from group consisting of
fluorine, chlorine, bromine, HO—, NC—, $F_3C$—, $HF_2C$—, $FH_2C$—, HO—$C_{1-6}$-alkyl-, $C_{1-6}$-alkyl-, $C_{1-6}$-alkyl-O—, and aryl-,
wherein the above-mentioned aryl of group may optionally be substituted independently of one another by one or more substituents selected from group consisting of fluorine, chlorine, bromine, NC—, $F_3C$—, $HF_2C$—, $FH_2C$—, HO—$C_{1-3}$-alkyl-, $C_{1-3}$-alkyl-, and $C_{1-3}$-alkyl-O—.

10. The compound according to claim 1, characterised in that
$R^6$, $R^7$ are selected from the group consisting of
$C_{1-6}$-alkyl-, $C_{3-6}$-cycloalkyl-, and $C_{3-6}$-cycloalkyl-$C_{1-3}$-alkyl-,
wherein the above-mentioned members of the group may optionally be substituted independently of one another by one or more substituents selected from the group consisting of
fluorine, HO—, NC—, $C_{1-3}$-alkyl-, and $C_{1-3}$-alkyl-O—.

11. The compound according to claim 1, characterised in that
$R^6$ is
$C_{5-6}$-cycloalkyl-,
wherein the above-mentioned $C_{5-6}$-cycloalkyl- may optionally be substituted by one or more substituents selected from the group consisting of
fluorine, and $H_3C$—.

12. The compound according to claim 1, characterised in that
$R^7$ is
$C_{1-4}$-alkyl-,
wherein the above-mentioned $C_{1-4}$-alkyl- may optionally be substituted by one or more substituents selected from the group consisting of
fluorine, HO—, and $H_3C$—O—.

13. The compound according to claim 1, characterised in that
$R^8$ is selected from the group consisting of
$C_{1-6}$-alkyl-, $C_{3-6}$-cycloalkyl-, and $C_{3-6}$-cycloalkyl-$C_{1-3}$-alkyl-,
wherein the above-mentioned members of the group may optionally be substituted independently of one another by one or more substituents selected from the group consisting of
fluorine, HO—, NC—, and $H_3C$—.

14. The compound according to claim 1, characterised in that
$R^9$ is selected from the group consisting of
H—, $F_3C$—$CH_2$— and $C_{1-6}$-alkyl-,
wherein the above-mentioned members of the group may optionally be substituted independently of one another by one or more
fluorines.

15. The compound according to claim 1, characterised in that
$R^{12}$ is selected from the group consisting of
$F_3C$—, $HF_2C$—, $FH_2C$—, $C_{1-6}$-alkyl-, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, and heteroaryl-$C_{1-6}$-alkyl-,
wherein the above-mentioned members of the group may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$—, HO—$C_{1-3}$-alkyl-, $C_{1-3}$-alkyl-, and $C_{1-3}$-alkyl-O—.

16. The compound according to claim 1, characterised in that
$R^{13}$ is selected from the group consisting of
H—, $F_3C$—$CH_2$—, $C_{1-6}$-alkyl-, $C_{3-7}$-cycloalkyl-, $C_{3-7}$-cycloalkyl-$C_{1-3}$-alkyl-, aryl-, aryl-$C_{1-3}$-alkyl-, heterocyclyl-, heterocyclyl-$C_{1-3}$-alkyl-, heteroaryl-, and heteroaryl-$C_{1-3}$-alkyl-,
wherein two $C_{1-6}$-alkyl groups bound to the same nitrogen atom may be joined together forming, together with the nitrogen atom to which they are bound, a 3 to 7 membered heterocyclic ring, and
wherein the above-mentioned members of the group may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$—, HO—$C_{1-6}$-alkyl-, $C_{1-6}$-alkyl-, and $C_{1-6}$-alkyl-O—.

17. The compound according to claim 1, characterised in that
$R^{14}$ is selected from the group consisting of
H—, $F_3C$—, $HF_2C$—, $FH_2C$—, $F_3C$—$CH_2$—, $C_{1-6}$-alkyl-, $C_{3-7}$-cycloalkyl-, $C_{3-7}$-cycloalkyl-$C_{1-3}$-alkyl-, aryl-, aryl-$C_{1-3}$-alkyl-, heterocyclyl-, heterocyclyl-$C_{1-3}$-alkyl-, heteroaryl- and heteroaryl-$C_{1-3}$-alkyl-,
wherein the above-mentioned members of the group may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$—, $C_{1-3}$-alkyl-, and $C_{1-6}$-alkyl-O—.

18. A pharmaceutical composition comprising at least one compound of formula I according to claim 1 and a pharmaceutically acceptable carrier.

* * * * *